US007192932B1

(12) United States Patent
Taskén et al.

(10) Patent No.: US 7,192,932 B1
(45) Date of Patent: Mar. 20, 2007

(54) USE OF IMMUNOMODULATING AGENTS

(75) Inventors: Kjetil Taskén, Rykkinn (NO); Einar M. Aandahl, Lillehammer (NO); Pål Aukrust, Ridabu (NO); Bjørn S. Skålhegg, Høvik (NO); Fredrik Müller, Olso (NO); Stig Frøland, Oslo (NO); Vidar Hansson, Sandvika (NO)

(73) Assignee: Lauras AS, Olso (NO)

( * ) Notice: Subject to any disclaimer, the term of this patent is extended or adjusted under 35 U.S.C. 154(b) by 0 days.

(21) Appl. No.: 09/428,458

(22) Filed: Oct. 28, 1999

Related U.S. Application Data

(63) Continuation of application No. PCT/NO98/00134, filed on Apr. 29, 1998.

(30) Foreign Application Priority Data

Apr. 29, 1997 (NO) ........................... 971977

(51) Int. Cl.
*A61K 31/70* (2006.01)
*C07H 19/00* (2006.01)
*C07D 273/00* (2006.01)

(52) U.S. Cl. .................. 514/43; 514/47; 514/261; 536/27.13; 536/27.14; 536/27.2; 544/264

(58) Field of Classification Search .............. 435/6, 435/7.1, 7.2; 514/46, 2, 44; 536/24.5
See application file for complete search history.

(56) References Cited

U.S. PATENT DOCUMENTS

| 4,568,676 A | 2/1986 | Smith |
| 5,276,017 A | 1/1994 | Feinberg |
| 5,843,916 A * | 12/1998 | Cho-Chung et al. .......... 514/47 |

FOREIGN PATENT DOCUMENTS

| WO | WO 9319766 | 10/1993 |
| WO | WO 93/21929 | * 11/1993 | .................. 514/44 |
| WO | WO 9321929 | 11/1993 |
| WO | WO 9416736 | 8/1994 |
| WO | WO 9704096 | 2/1997 |
| WO | WO 9711171 | 3/1997 |

OTHER PUBLICATIONS

Bjorn T. Gjertsen et al., Novel (Rp)-cAMPS Analogs as Tools for Inhibition of cAMP-kinase in Cell Culture. The Journal of Biological Chemistry, vol. 270, No. 35, pp. 20599-20607, Sep. 1, 1995.*
C.C. Chinery et al., Department of General Surgery.*
Punch et al. Opposite Modulation of Opiate Withdrawal Behaviors on Microinfusion of a Protein Kinase A Inhibitor Versus Activator into the Locus Coeruleus or Periaqueductal Gray. The Journal of Neuroscience. Nov. 1, 1997, vol. 17, No. 21, pp. 8520-8527.*
Jackson, William Pharmacology 1996, 52:226-234.*
Ogreid et al., (Rp)- and (Sp)-8-piperidino-adenosine 3',5'-(cyclic)thiophosphates discriminate completely between site A and B of the regulatory subunits of cAMP-dependent protein kinase type I and II, 1994, Eur J Biochem., 221(3), pp. 1089-1094.*
Gjertsen et al., Novel (Rp)-cAMPs Analogs as Tools for Inhibition of cAMP-kinase in Cell Culture, 1995, The Journal of Biological Chemistry, vol. 270, No. 35, pp. 20599-20607.*
Hofmann et al., Restoration of T-cell function in HIV infection by reduction of intracellular cAMP levels with adenosine analogues, 1993, AIDS, vol. 7, No. 5, pp. 659-664.*
Mochly-Rosen, *Science*, 268:247-251 (1995).
Skålhegg et al, *Science*, 263:84-87 (1994).
Levy et al, *Eur. J. Immunol*, 26:1290-1296. (1996).
Torgersen et al, *J. Biol. Chem.*, 272(9):5495-5500 (1997).
Skalhegg et al, *Frontiers in Bioscience 2*, pp. d331-342 (1997).
Hofmann et al, *AIDS*, 7:659-664 (1993), pp. 659 and 663 Only.
Øgreid et al, *European J. of Biochem.*, 227:1089-1094 (1994).
Dostmann et al, *J. of Biological Chemistry*, 265(18)10484-10491 (1990).
Cho-Chung, *Antisense Nucleic Acid Drug Dev.*, 6(3)234-244 (1996 Fall), Abstract Only.
Hoffman et al, *AIDS*, 7:659-664 (1993).
Skålhegg et al, *J. of Biological Chemistry*, 267(22):15717-15714 (1992).

* cited by examiner

*Primary Examiner*—James Schultz
*Assistant Examiner*—Amy Bowman
(74) *Attorney, Agent, or Firm*—Sughrue Mion, PLLC

(57) ABSTRACT

Pharmaceutical compositions useful for treating immunosuppressive disease and containing compounds capable of inhibiting cAMP-dependent protein kinase A (PKA) as well as use of the same, are described.

4 Claims, 15 Drawing Sheets

Figure 2A:
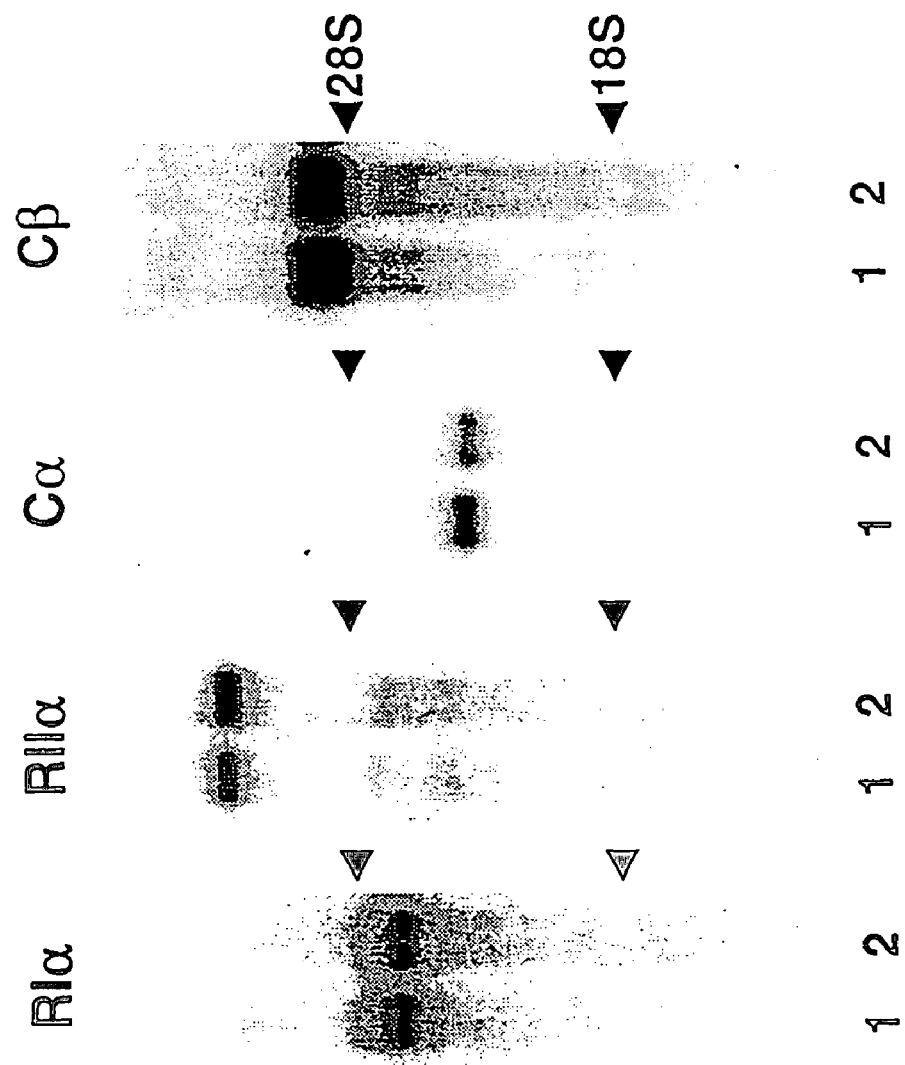

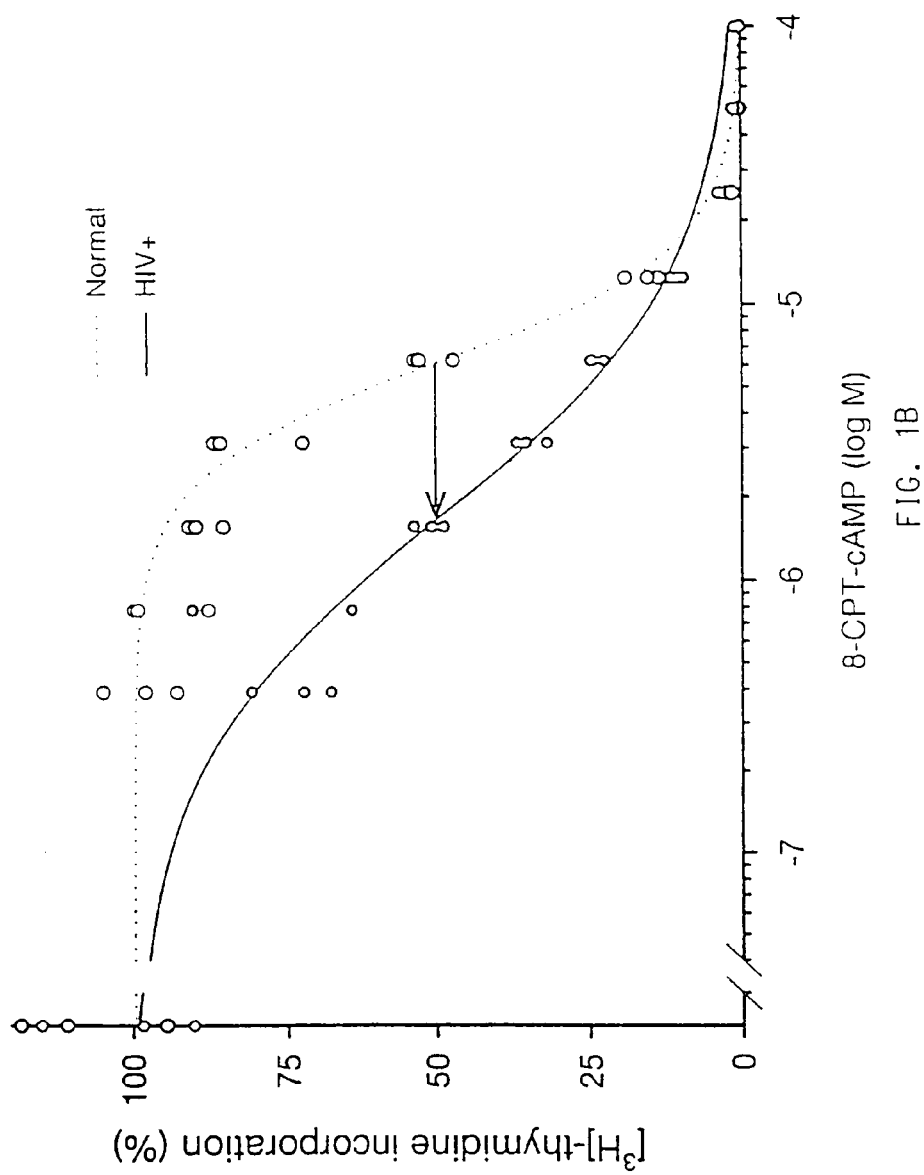
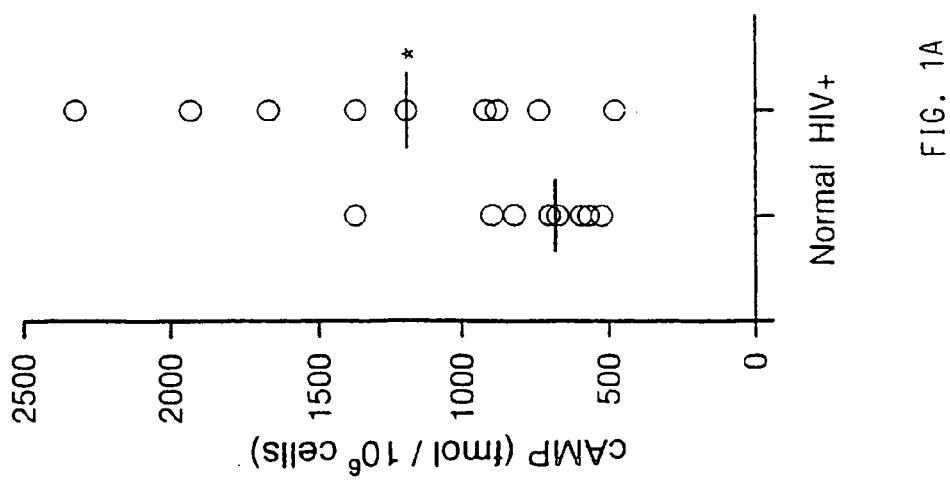
FIG. 1B
FIG. 1A

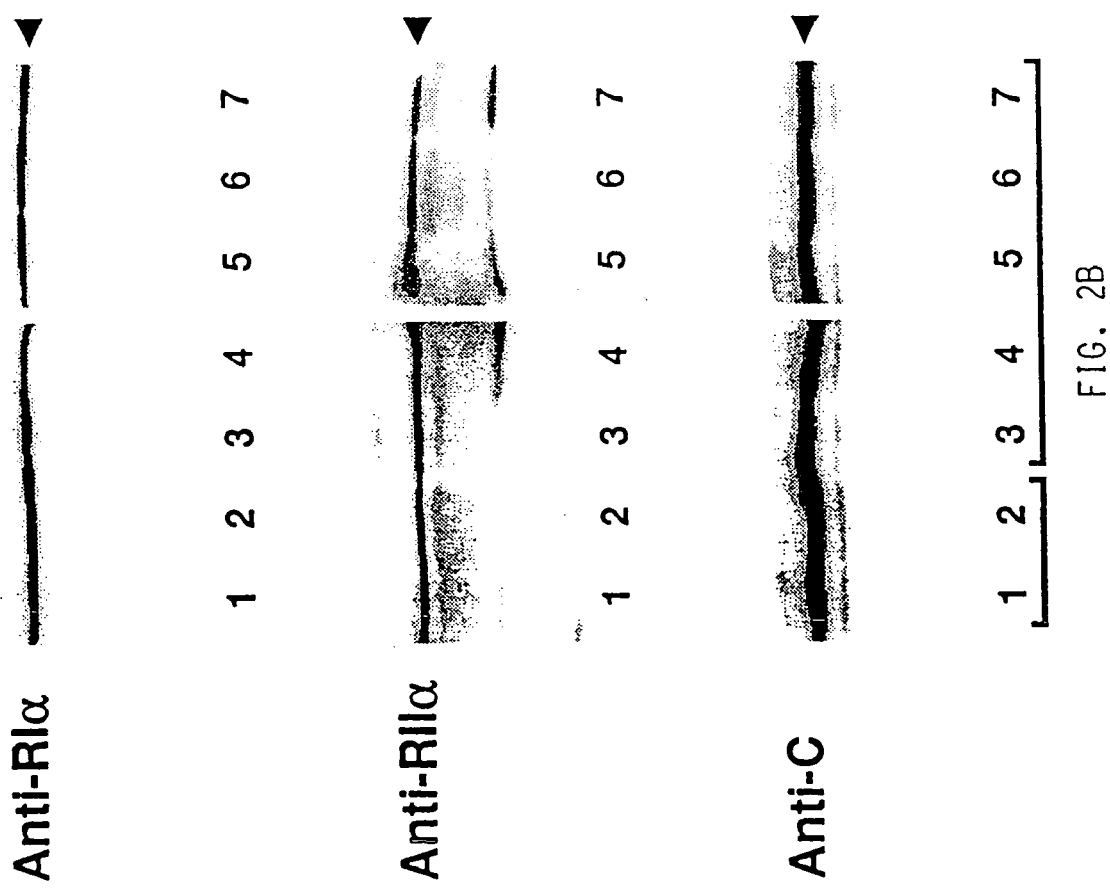

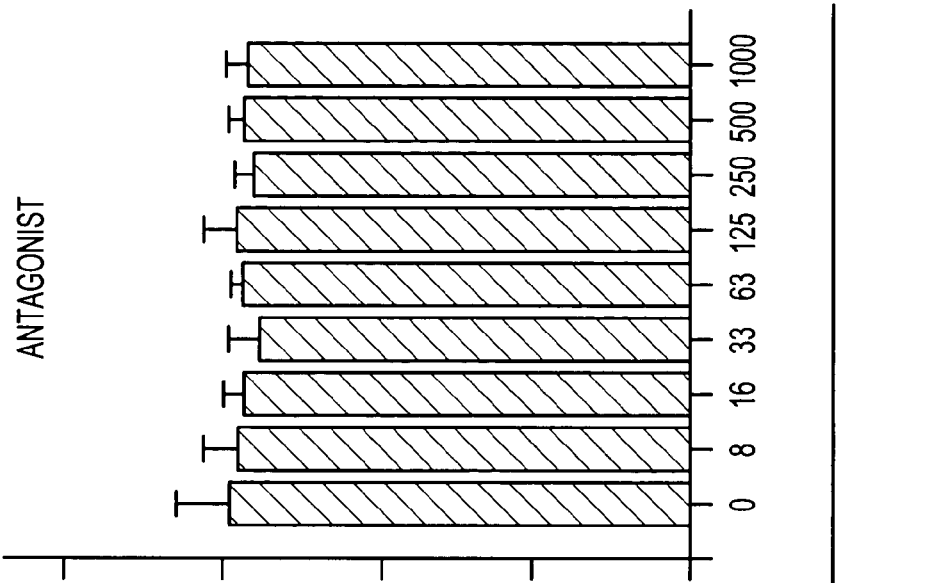
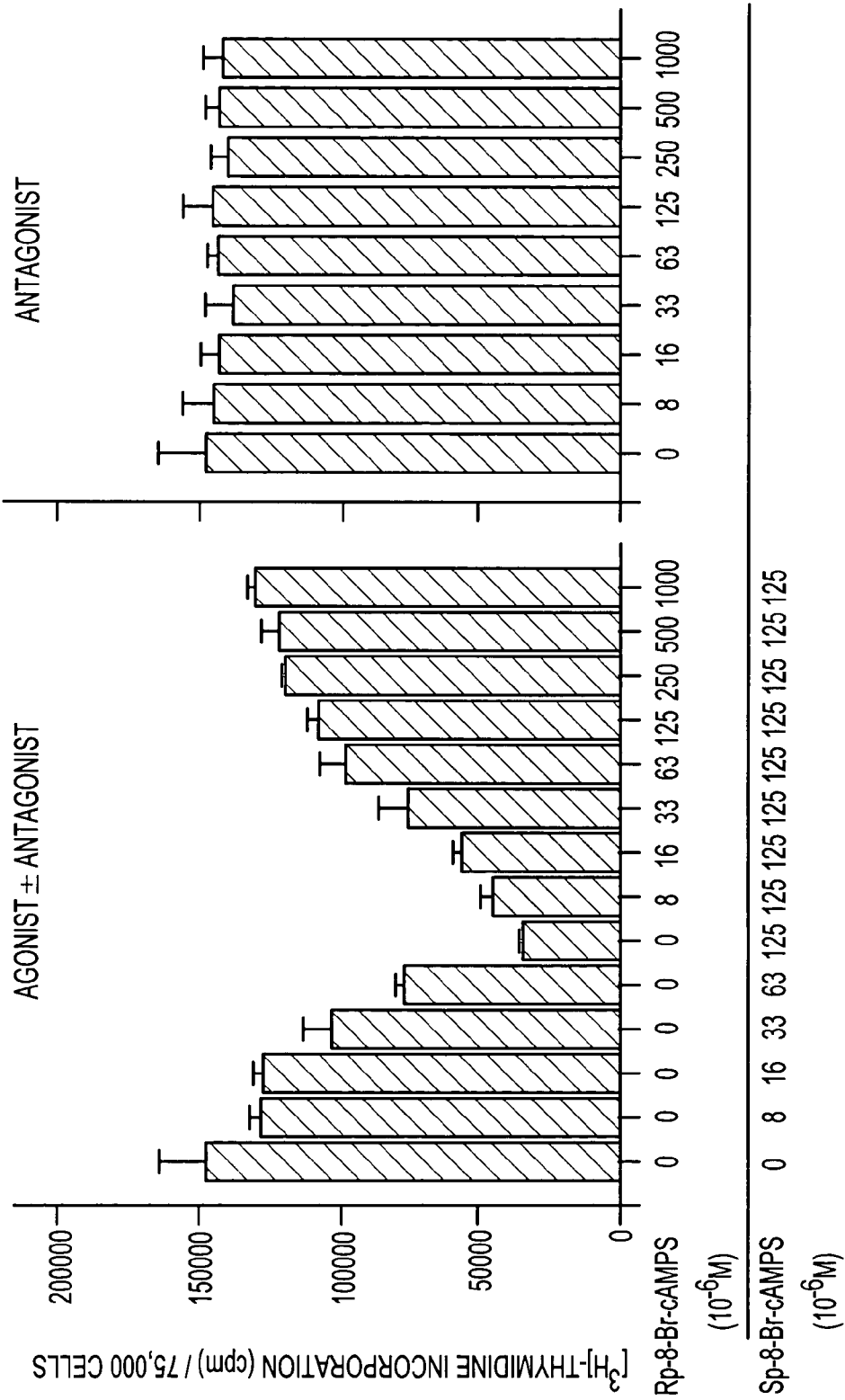

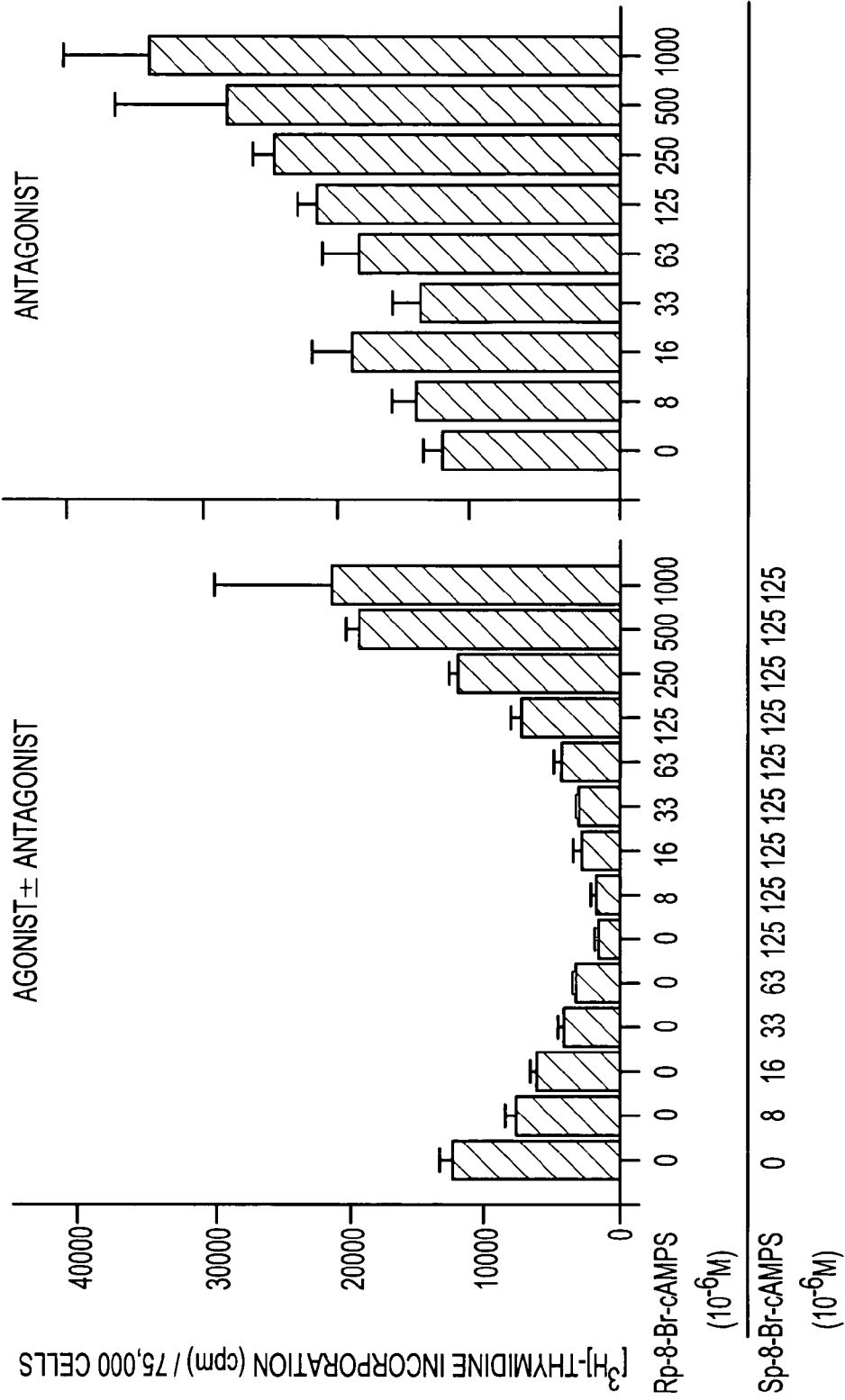

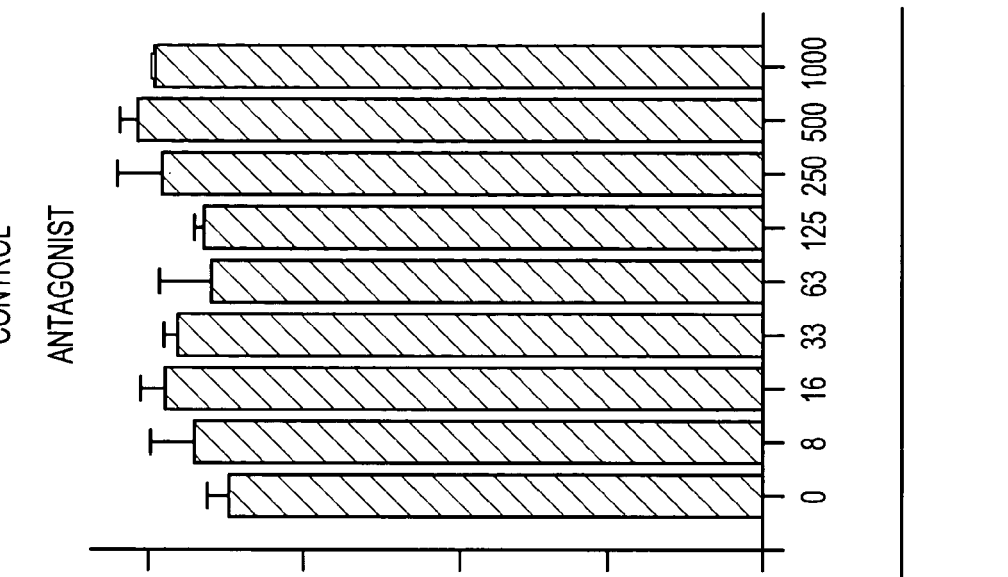
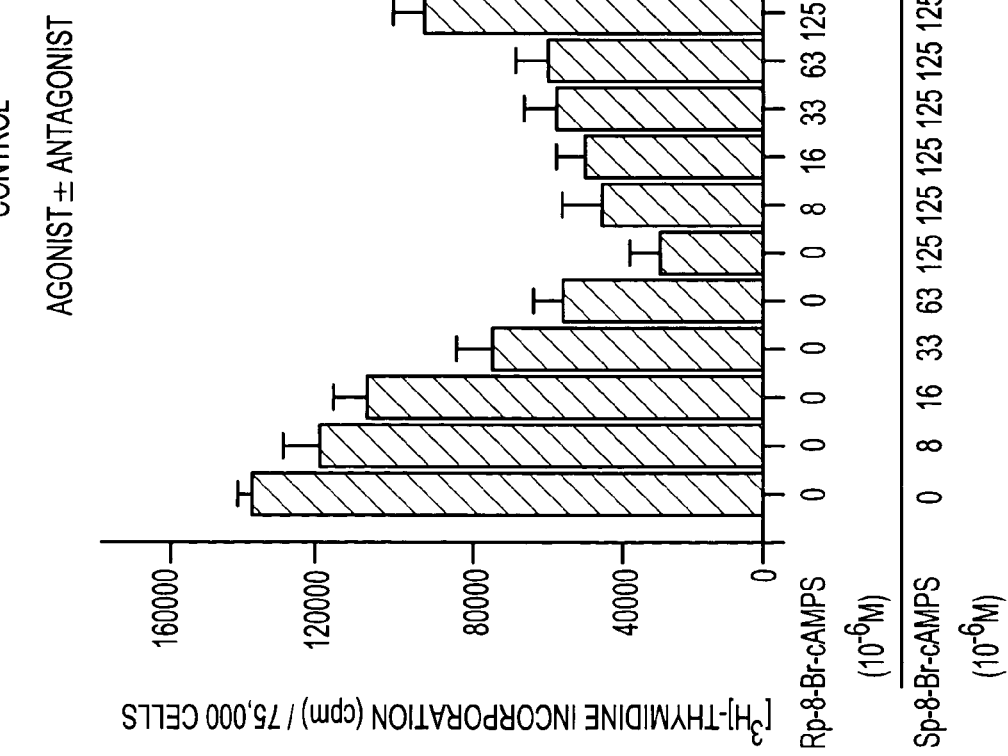

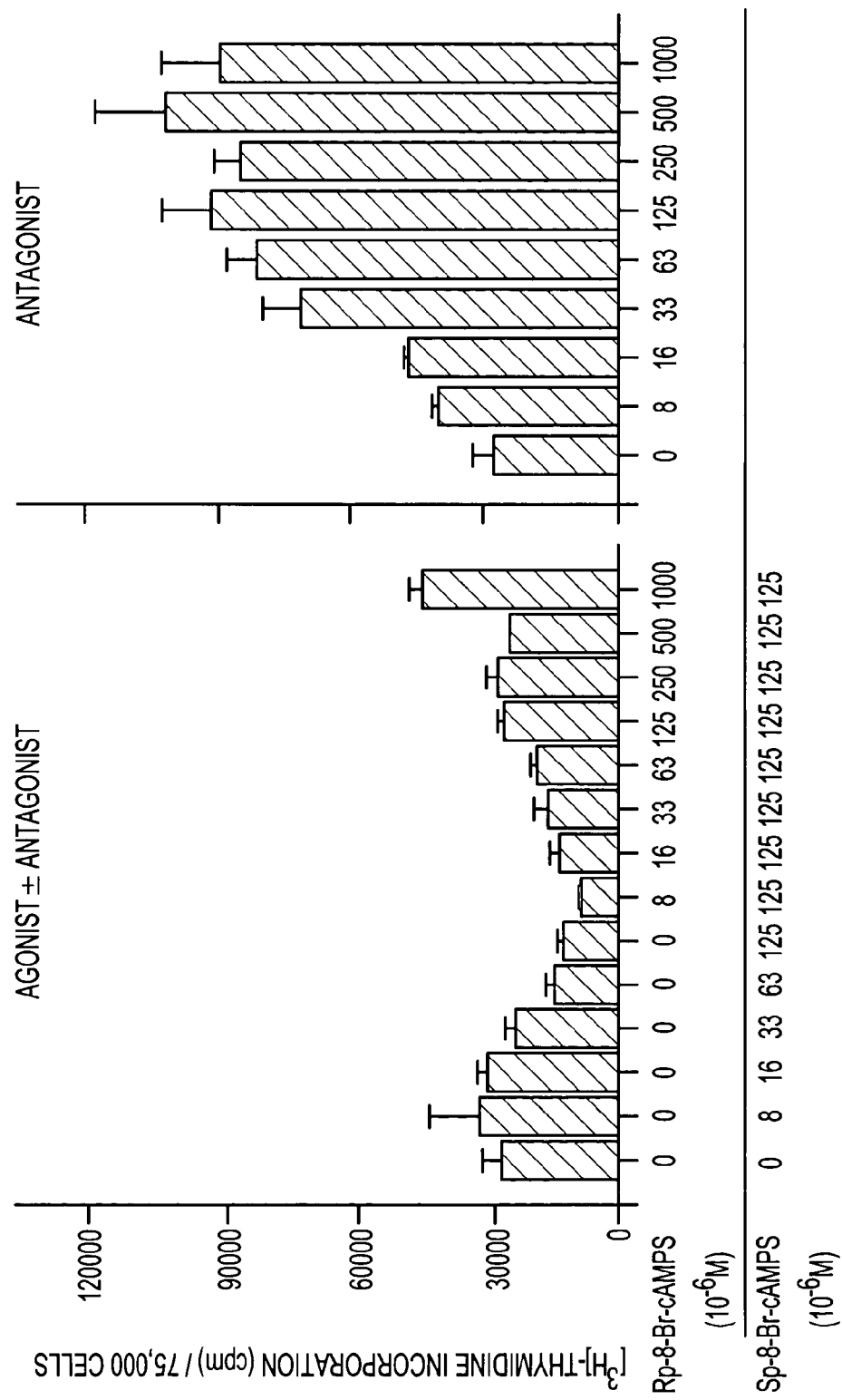

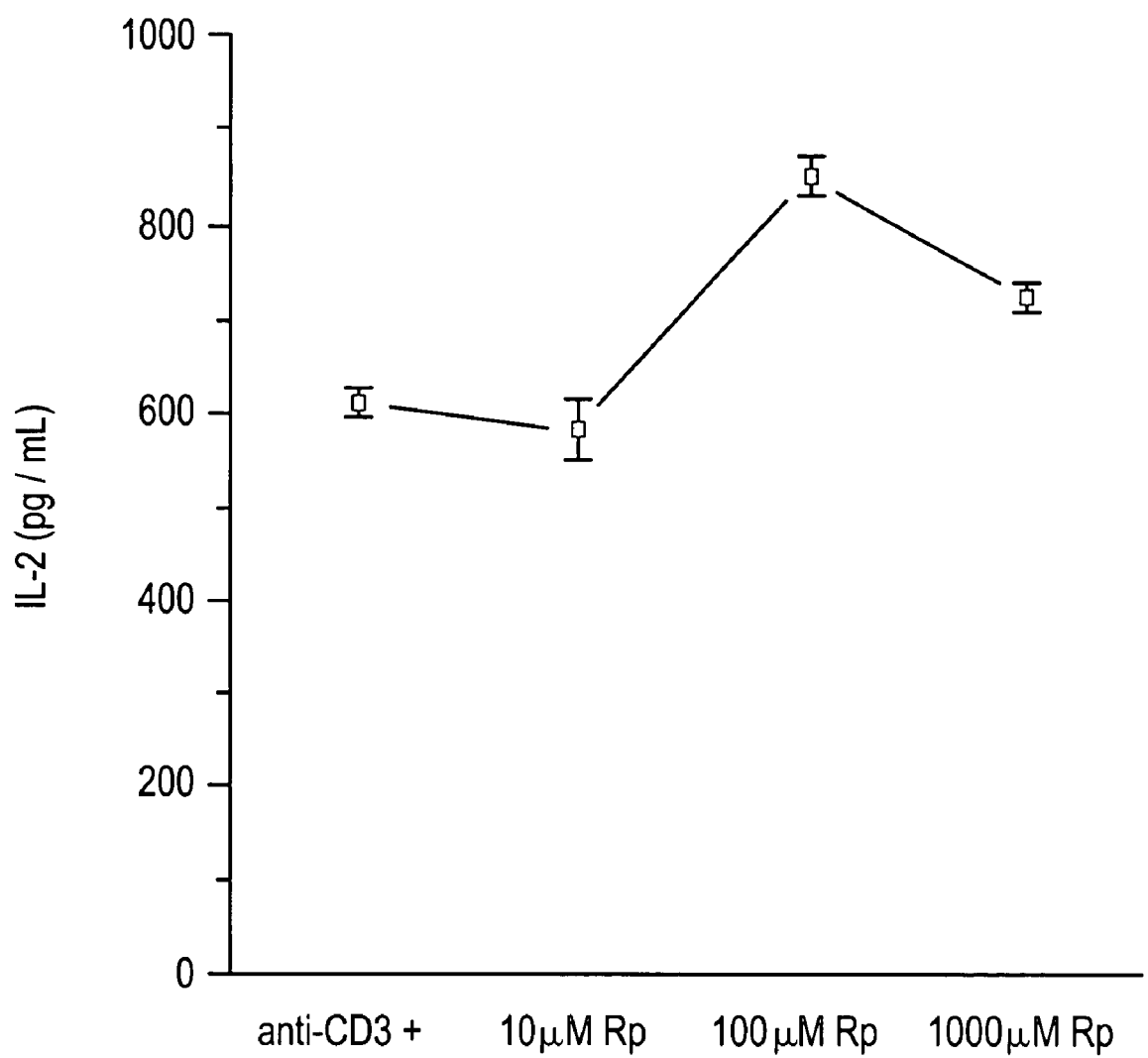

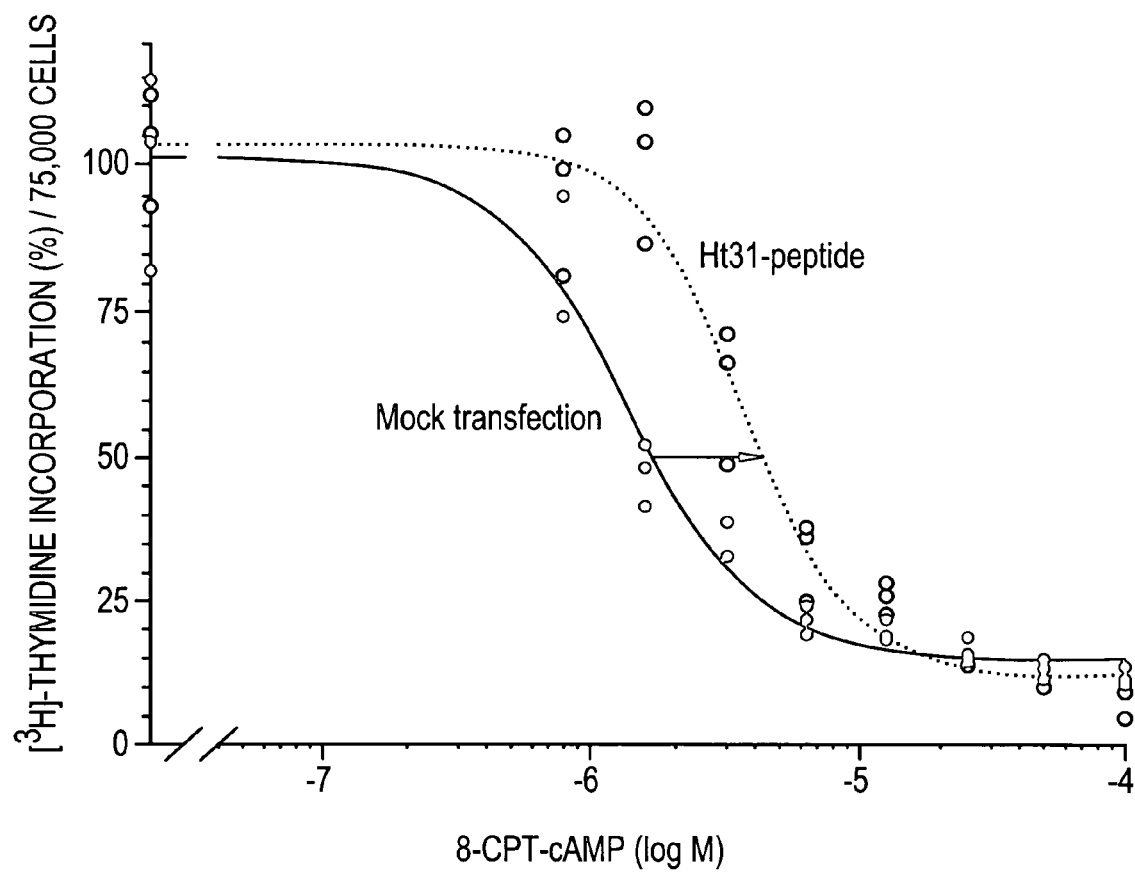

US 7,192,932 B1

SEQUENCE LISTING

<160> NUMBER OF SEQ ID NOS: 8

<210> SEQ ID NO 1
<211> LENGTH: 22
<212> TYPE: PRT
<213> ORGANISM: synthetic construct

<400> SEQUENCE: 1

Asp Leu Ile Glu Glu Ala Ala Ser Arg Ile Val Asp Ala Val Ile Glu
 1               5                   10                  15

Gln Val Leu Ala Ala Tyr
            20

<210> SEQ ID NO 2

```
<211> LENGTH: 24
<212> TYPE: PRT
<213> ORGANISM: synthetic construct

<400> SEQUENCE: 2

Asp Leu Ile Glu Glu Ala Ala Ser Arg Ile Val Asp Ala Val Ile Glu
 1               5                  10                  15

Gln Val Lys Ala Ala Gly Ala Tyr
             20

<210> SEQ ID NO 3
<211> LENGTH: 24
<212> TYPE: PRT
<213> ORGANISM: synthetic construct

<400> SEQUENCE: 3

Gln Val Ile Ser Glu Ala Thr Gln Val Leu Ala Thr Thr Val Gly Lys
 1               5                  10                  15

Val Ala Gly Arg Val Cys Gln Ala
             20

<210> SEQ ID NO 4
<211> LENGTH: 40
<212> TYPE: PRT
<213> ORGANISM: synthetic construct

<400> SEQUENCE: 4

Val Gln Gly Asn Thr Asp Glu Ala Gln Glu Glu Leu Ala Trp Lys Ile
 1               5                  10                  15

Ala Lys Met Ile Val Ser Asp Val Met Gln Gln Ala His His Asp Gln
             20                  25                  30

Pro Leu Glu Lys Ser Thr Lys Leu
         35                  40

<210> SEQ ID NO 5
<211> LENGTH: 39
<212> TYPE: RNA
<213> ORGANISM: synthetic construct

<400> SEQUENCE: 5
guacugccac ugaugaguccc gugaggacga aacuccaug                    39

<210> SEQ ID NO 6
<211> LENGTH: 45
<212> TYPE: RNA
<213> ORGANISM: synthetic construct

<400> SEQUENCE: 6
ggcgguacug ccacugauga guccgugagg acgaaacucc augga              45

<210> SEQ ID NO 7
<211> LENGTH: 18
<212> TYPE: DNA
<213> ORGANISM: synthetic construct

<400> SEQUENCE: 7
gtactgccag actccatg                                            18

<210> SEQ ID NO 8
<211> LENGTH: 24
<212> TYPE: DNA
<213> ORGANISM: synthetic construct
```

```
<400> SEQUENCE: 8
ggcggtactg ccagactcca tggt                                              24
```

USE OF IMMUNOMODULATING AGENTS

This Appln is a Con of PCT/NO98/00134 Apr. 29, 1998

The present invention relates to use of inhibitors abolishing the function of cAMP dependent protein kinase A, type I to produce a pharmaceutical to treat immuno-suppressive diseases.

BACKGROUND OF THE INVENTION

The immune system of mammals has evolved different strategies to defend the organism against the variety of potentially infectious agents. The ability to acquire specific and anamnestic responses against intruders features the adaptive immune system. Main players in the adaptive immune system are B and T lymphocytes, and the specific recognition of antigen by these cells is mediated by receptors with some degree of structural similarity, yet functionally very different. The different receptor specificities are made possible through somatic rearrangement of a limited number of genes and are clonally distributed. The main strategy of this system is to generate a nearly unlimited number of specificities to cover the recognition of almost any foreign antigen. Immunological memory is partly a result of clonal expansion of subsets of T and B cells reacting with a particular antigen, and enables the organism to respond more quickly at the second encounter with the same anti gen.

Cell proliferation is used as a parameter for immune activation. According to the clonal selection theory, exposure to antigen leads to activation of individual B and T cell clones with corresponding receptor-specificities. However, the number of cells with affinity for a certain antigen is a small fraction of the total number of cells (~0,001%). It is therefore crucial that the activated cells are capable of proliferation (clonal expansion) in order to generate an adequate immune response. Thus, proliferation is a very important parameter characterizing lymphocyte function and capability of immune activation. In in vitro experiments, it is possible to activate the total population of isolated T lymphocytes by using antibodies directed against the antigen receptor complex (TCR/CD3). This will mimic the in vivo situation when T cells are immunoactivated to clonal expansion through the antigen receptor. It is known that T cell proliferation is inhibited through the cAMP signalling, pathway.

Cyclic AMP-dependent protein kinase (PKA) is an enzyme present in all cells. Hormones and neurotransmitters binding to specific receptors stimulate the generation of the second messenger 3',5'-cyclic adenosine monophosphate (cAMP). Cyclic AMP is one of the most common and versatile second messengers and exerts its action by binding to and activate PKA. PKA is a serine/threonine protein kinase which phosphorylates a number of different proteins within a cell, and thereby regulates their activity. It is known that PKA regulates a vast variety of cellular processes such as metabolism, proliferation, differentiation and regulation of gene transcription. PKA is made up of four different subunits, a regulatory (R) subunit dimer and two catalytic (C) subunits. Furthermore, two main classes of PKA isozymes, PKA type I and PKA type II (PKAI and PKAII, respectively) have been described. PKAI and PKAII can be distinguished due to their R subunits, designated RI and RII. Isoforms of RI and RII are called RI$\alpha$, RI$\beta$, RII$\alpha$, RII$\beta$. Moreover, the C subunits also exist as isoforms referred to as C$\alpha$, C$\beta$ and C$\gamma$. The different subunits may form multiple forms of PKA (isozymes) potentially more than 18 different functions.

PKA is a key negative regulator of lymphocyte function. The present inventors and other have shown that cAMP inhibits T lymphocyte proliferation induced through the T cell antigen receptor/CD3 complex (TCR/CD3). We have shown that T cells express both PKAI and PKAII. However, only the selective activation of PKAI is sufficient to mediate the inhibitory effect of cAMP. In addition we have demonstrated that PKAI, but not PKAII, redistribute to, colocalize with and inhibit signalling through antigen receptors on T and B cells and natural killer cells and regulate mitogenic responses in T and B cells and acute cytotoxic responses in NK cells. Thus, PKAI serve as a key negative regulator of lymphocyte functions e.g. mitogenic and cytotoxic responses initiated through antigen receptors.

HIV and Common variable immunodeficiency (CVI). Both primary and secondary immunodeficiencies cause an increased incidence of opportunistic infections and cancer, and are increasing causes of morbidity and mortality in all parts of the world. Human immunodeficiency virus (HIV) causes a chronic infection leading to severe dysfunction of the immune system with markedly increased incidence of a large number of infections and certain forms of malignancies (e.g. lymphoma and Kaposis' sarcoma). In many communities in USA, HIV infection is the leading cause of death among "young" adults. In the developing world this problem is even larger. Next to immunoglobulin (Ig) A deficiency, common variable immunodeficiency (CVI) is the most frequent type of primary immunodeficiency. This form of primary hypogammaglobulinaemia is characterized by onset of immunodeficiency after the first two years of life, by severely decreased serum IgG level and recurrent bacterial infections, particularly in the respiratory tract.

Cellular defects in immunodeficiencies. T cell dysfunction is the immunologic hallmark of HIV infection. Defective lymphocyte cytokine production and impaired proliferative response on stimulation are early signs of immunodeficiency in these patients, manifested even before a decline in CD4+ lymphocyte counts is observed. B cell dysfunction with impaired antibody synthesis is the major immunologic characteristic of CVI patients. However, the immunologic abnormalities in CVI are not restricted to B cells, but often also involve T cell dysfunction, e.g. impaired proliferative response on stimulation. The B cells in CVI patients are not necessarily intrinsically defective, and impaired T cell "help" may be of importance for the B cell defect in these patients. T cell dysfunction may also be of importance for certain clinical manifestations in these patients not necessarily related to defective antibody production, e.g. increased incidence of granulomata and malignancies.

Current therapies. Antiretroviral therapy is the main component in the treatment of HIV-infected patients. However, although potent antiretroviral combination therapy may markedly increase the CD4+ and CD8+ lymphocyte counts in HIV-infected patients, impaired T cell function seems to persist, as indicated in the observations made in Example 1, tables I and 2B. Thus, there is a need for immunomodulating, agents in addition to antiretroviral therapy in these patients. Immunoglobulin substitution is the main component in the treatment of CVI patients. However, this substitution therapy does not restore the defective T and B cell function. Furthermore, in some clinical complications, e.g. noncaseating granulomata and persistent viral infections, there is need for therapy which more directly may exchange T cell function.

Therapeutic potential of novel drugs targeting T cell dysfunction. Although impaired T cell function is a well recognized immunologic feature of both HIV infection and CVI, the exact molecular mechanism for this T cell impairment is unknown. Therapeutical modalities directed against such intracellular defects may be of major importance in the treatment of these patients, and may have the potential to restore important immunologic defects in HIV-infected patients and in patients with CVI.

Hofmann et al. (Aids, Vol 7; 659–664, 1993) and WO 9-3/19766 has demonstrated that HIV-seropositive individuals without AIDS showed significant increase in intracellular cAMP levels and PKA activity in crude peripheral blood mononuclear cells (PBMC) from HIV-seropositive subjects. Examination of T cells was reported as data not shown and did not reach significance because of larger variability, probably induced by the T cell purification method. Their study further indicated that adenosine analogues such as 2',5' dideoxyadenosine (ddAdo) reduced cellular cAMP levels in PBMC and increased the cell proliferation. This effect was, however, concentration dependent such that concentrations in the range of 6 ng/ml were effective and higher concentrations were suppressive or did not further inhibit cAMP levels. It was not demonstrated similar effects in the T cells sampled from HIV-patients, neither a simple concentration/response relationship. They have used purified T cells in their examples but these cells were sampled from healthy blood donors and purified by positive selection that may lead to premature T cell activation.

Chu-Chung, Y S, Genieser H and Jastorff, B (WO 93)/21929-A) have shown treatment applied to cancer cells by antagonising cAMP-dependent protein kinases, by using phosphorothoate derivatives of cAMP.

In summary it is not known in the prior art the role of the cAMP level in T cells regarding cell proliferation and immune response during physiological conditions. Furthermore, it is not known the role of the protein kinase isoenzymes regarding T cell functions during physiological conditions and if cAMP/PKAI has immunomodulating activity. Although the results of Hofman et al (vide supra) suggested increased cAMP level in mononuclear cells, it was not presented documentation supporting a similar condition in T cells. It is thus not known if the cAMP level is increased in purified T cells and negatively selected (not activated) T cells from HIV+ subjects, and nothing regarding the cAMP/PKA pathway in patient suffering from CVI.

SUMMARY OF THE INVENTION

It is therefore the object of the present invention to specifically increase the T cell immune function and reverse T cell dysfunction in human immunodeficiency virus infected and common variable immunodeficiency patients by using suitable compounds interfering with the cAMP/PKA pathway in the T cells. Furthermore, as the role of PKA type I as an immuno modulator is shared among all lymphoid cells (T cells, B cells, NK cells) disruption of the cAMP/PKA pathway may pertain also to B and NK cells.

This object is obtained by the present invention characterized by the enclosed claims.

DETAILED DESCRIPTION OF THE INVENTION

Disruption of effects mediated by cAMP dependent protein kinase can be performed in the following ways:

PKA isozyme-specific cAMP antagonists. The activity of PKA is specifically regulated through the R subunit by cAMP in vivo. Chemically modified, diffusible cAMP analogs can be used to manipulate intracellular levels of cAMP. Thiosubstituted analogs where the phosphorous in the cyclic phosphate of cAMP has been exchanged with sulfur, produces a compound resistant to breakdown by phosphodiesterases. Furthermore, thio-substituted analogs can have two forms; the sulfur may be in an equatorial or axial position versus the adenine ring. Whereas the axial diastereomer (Sp-cAMP-phosphorothioate, Sp-cAMPS and derivatives) serves as a cAMP agonist, the equatorial diastereomer (Rp-cAMP-phosphorothioate, Rp-cAMPS and derivatives) binds competetively to the cAMP binding sites of the R subunits, but does not activate the enzyme. A more detailed characterization demonstrated that Rp-cAMPS works as a full antagonist of PKAI isozymes only ($RI\alpha_2C_2$, $R_{12}C_2$) and as a partial agonist of PKAII isozymes ($RI\alpha_2C_2$, $RII\beta_2C_2$). Examples of diffusible derivatives of Rp-cAMPS useful in living cells are Rp-8-Br-cAMPS, Rp-8-Br-monobutyryl-cAMPS, Rp-monobutyryl-cAMPS, Rp-8-Cl-cAMPS, Rp-8-(4-chlorophenyl-thio)-cAMPS, Rp-piperidino-cAMPS.

Gene function knock out strategies. Effects mediated by specific isozymes of PKA can be disrupted by inhibition of synthesis of subunits of that enzyme complex. This can be accomplished by the use of sequence-specific antisense oligonucleotides hybridizing, to mRNA and blocking, translation for subunits of PKA. Another strategy is to use hammerhead ribozymes specifically recognizing and cleaving mRNA for subunits of PKA to inhibit synthesis of these subunits.

Ribozymes. Ribozymes are RNA molecules which catalyse the cleavage and formation of phosphodiester bonds. The discovery of short oligoribonucleotides with endoribonuclease activity has provided researchers with an important tool to block expression of specific genes. The hammerhead domain is a good candidate for incorporation in gene-specific antisense transcripts and induces a enzymatic cleavage at a targeted GUC-sequence in the mRNA and disrupts subsequent translation of the mRNA to protein. Ribozyme can be transfected into cells as RNA or introduced as minigenes from which the ribozyme is transcribed intracellularly under control of a promotor. Furthermore, ribozymes can be chemically modified by addition of alkyl groups in 2-position of the ribose moiety to increase the permeability or intracellular effects can be prolonged by substitution with 2-deoxy-cytosine or 2-deoxy-uracil.

Sequence-specific antisense oligonucleotides. Oligonucleotides antisense to specific mRNAs will bind to RNA in a DNA/RNA heteroduplex and inhibit translation of mRNA to protein by blocking the movement and reading by the translation machinery. Thio-substituted analogs are more stable to degradation and can be transfected to block translation of specific genes.

Disruption of anchoring. Specific cAMP-mediated effects at defined subcellular loci have been shown to be dependent on anchoring of PKA type II via hydrophobic interaction with an amphipatic helix domain in A kinase anchoring proteins (AKAPs) in close proximity to substrate at that subcellular location. Disruption of anchoring by 22-amino acid competition peptides to the interaction domain introduced by liposome mediated peptide transfer, has been shown to abolish isozyme-specific effects mediated by PKA type II. No similar effects has as of yet been shown for PKA type I. Example of AKAP-competitor peptides are 22-mer H₂N-Asp-Leu-Ile-Glu-Glu-Ala-Ala-Ser-Arg-Ile-Val-Asp-Ala-Val-Ile-Glu-Gln-Val-Lys-Ala-Ala-Tyr-COOH, (SEQ. ID. NO 1)

H₂N-Asp-Leu-Ile-Glu-Glu-Ala-Ala-Ser-Arg-Ile-Val-Asp-Ala-Val-Ile-Glu-Gln-Val-Lys-Ala-Ala-Gly-Ala-Tyr-COOH, (SEQ. ID. NO 2)

H₂N-Gln-Val-Ile-Ser-Glu-Ala-Thr-Gln-Val-Leu-Ala-Thr-Thr-Val-Gly-Lys-Val-Ala-Gly-Arg-Val-Cys-Gln-Ala-COOH, -(SEQ. ID. NO 3) and H₂N-Val-Gln-Gly-Asn-Thr-Asp-Glu-Ala-Gln-Glu-Glu-Leu-Ala-Trp-Lys-Ile-Ala-Lys-Met-Ile-Val-Ser-Asp-Val-Met-Gln-Gln-Ala-His-His-Asp-Gln-Pro-Leu-Glu-Lys-Ser-Thr-Lys-Leu-COOH (SEQ. ID. NO 4).

According to the invention, disruption of the cAMP-induced inhibition of T cell immune responses can be obtained by abolishing, PKA type I/RIα. Then hammerhead ribozymes to PKA type I RIα have been synthesised, tested in vitro and shown to be fully active following transfection of peripheral blood T cells. Functional consequences of ribozyme treatment will be measured as anti-CD3 induced proliferation we will demonstrate reversal of sensitivity to CAMP.

Example of hammerhead ribozymes designed to knock-out the RIα subunit of PKA type I are GUACUGCCACUGAUGAGUCCGUGAGGAC-GAAACUCCAUG (SEQ. ID. NO 5) and

GGCGGUACUGCCACUGAUGAGUC-CGUGAGGACGAAACUCCAUGGA (SEQ. ID. NO 6).

Example of antisense oligo: to RIα:

GTACTGCCAGACTCCATG (SEQ. ID. NO 7) and

GGCGGTACTGCCAGACTC CATGGT (SEQ. ID. NO 8)

These antisense nucleotides comprise the target sequences of the hammerhead ribozymes.

Disruption of anchoring has previously been shown for PKA type II translocation, but not for PKA type I. By cloning PKA type I anchoring proteins we have used far-western technique employing RIα as the probe on screenings of blood cell expression libraries. Furthermore, we are employing, a yeast two-hybrid system to detect interacting proteins. The binding domains are characterized by deletional mapping and mutation analysis. Competitor peptides and transfection vectors directing expression of soluble fragments of AKAPs are designed.

Based on previous observations made and published by inventors (2, 3) activation of protein kinase A type I (and not type II isozymes) is necessary and sufficient to mediate cAMP-dependent inhibition of immune functions such as T and B cell proliferation induced through the antigen receptor or NK cell cytotoxicity mediated by specific NK receptors. Furthermore, protein kinase A type I redistributes to and colocalizes with the antigen receptor complex upon activation and capping of T and B cells (3). This anchoring of protein kinase A type I supports a role for this specific isozyme in modulation of immune responses mediated through receptors on lymphoid cells.

Discoveries by the inventors made in relation to the present invention show that there is an increased activation of protein kinase A type I in T cells from patients with HIV infection or CVI. It is further demonstrated that activation of this isozyme of PKA leads to an inhibition of immune function that can be reversed by selectively inhibiting the type I and not the type II isozymes of PKA. Based on these findings, the invention can be summarized as use of compounds aimed at reversing the inappropriate activation of protein kinase A type I in immunodeficiencies (HIV, CVI) and thereby restore T cell function and immune responsiveness. The enclosed examples show that the following formulations will all interact with signalling through protein kinase A type I and that they can be used separately or in combination in order to target and abolish the inappropriate activation of protein kinase A type I.

Formulations/compounds that will act as inhibitors of protein kinase A type I function:

1) Using, protein kinase A type I selective, competitive, full antagonists of cAMP, the ligand-dependent activation of protein kinase A type I, but not protein kinase A type II is inhibited (Examples 1, 2).

2) Using antisense oligonucleotides or ribozymes, protein kinase A type I function is inhibited by removing this isozyme of PKA (Examples 3).

3) Using competitor peptides that will displace protein kinase A type I from its anchoring with the antigen receptor complex, protein kinase A type I function is inhibited by removal of the activated enzyme from substrates in the antigen receptor complex that are relevant for inhibition of immun functions in T cells (Examples 4).

Thus, according to the present inventions inhibitors are used, which abolishes the function of cAMP dependent protein kinase A, type I to produce pharmaceutical preparations to treat immunosuppressive diseases.

The active chemical compound(s) are administered to a patient in need of treatment via all systemic administration routes known in the art. Consequently the medicament according to the invention is composed of active chemical ingredients, adjuvants, pharmaceutically acceptable fillers and comprises tablets, suppositories, injection fluids, infusion fluids and powder for production of any choice of administration form. Furthermore, the active compound(s) (ribozyme, protein) are expressed intracellularly as gene product(s), the expression of which are directed from gene(s) introduced into cells of interest. Gene expression is directed from a promoter active in the cells of interest and may be inserted in any form of linear or circular DNA vector for incorporation in the genome, independent replication or transient transfection/expression. Delivery of DNA vectors may be accomplished by all methods known in the art.

The requirements for a compound which is directed to modify the T cell cAMP-PKA pathway are at least diffusibility into the T cells and resistance to breakdown by phospho-diesterases. The present invention have demonstrated that a derivative of Rp-cAMP, such as Rp-8-Br-cAMPS in vitro, specifically increased the proliferation of purified T cells from HIV positive patients and in patients with common variable immunodeficiency. It was an especially surprising finding that when the anti-CD3-induced and greatly reduced proliferation of T cells from a HIV patient was investigated, the inventors observed that not only did the use of the antagonist Rp-8Br-cAMPS reverse the effect of the complementary cAMP agonist, but further increased the proliferation above the levels in untreated cells. Within the concentration range used (0–1000 mM) the T cell proliferation, expressed by [3H]-thymidine incorporation, correlated with the concentration. No increased T cell proliferation by using the cAMP antagonist was demonstrated in normal subjects.

The invention is in the following described in further detail by examples and figures, wherein

BRIEF DESCRIPTION OF THE EMBODIMENTS

FIG. 1. (A) of endogenous cAMP in peripheral blood CD3+ T cells from normal healthy blood donors (n=10) and HIV-infected patients (n=9). Levels of endogenous cAMP were examined in peripheral blood CD3+ T cells from normal healthy blood donors (n=10) and HIV-infected patients (n=9). CM+ T cells were isolated at 4 C by negative selection. Median values (horizontal line) and single patient data (open circles) are shown. * denotes p<0.05. (B) TCR/CD-3 stimulated proliferation of peripheral blood CM+ T cells from normal healthy blood donors and HIV-infected patients was assessed as [JH]-thymidine incorporation in the presence of increasing concentrations of 8-(4-chlorophenylthio)cAMP (8-CPT-cAMP). Curve-fit analyses were performed and $IC_{50}$ values calculated (see Table 1 and 2a for statistics and single patient data). Normalized levels of proliferation of T cells from a healthy blood donor (open circles) and a representative HIV-infected patient (solid circles, patient #10 in Table 2a) are shown ($IC_{50}$ values 6.11 μM vs. 1.78 μM). Note: Leftshift of $IC_{50}$ (arrow) and altered curve slope. The maximal levels of proliferation were drastically decreased in T cells from HIV-infected patients (see Table 1).

FIG. 2. Levels of protein kinase A. (A) Northern blot analyses of mRNA levels of PKA-subunits in normal blood donors (lane 1) and symptomatic HIV-infected patients (lane 2). Total RNA was extracted and subjected to northern blot analyses (20 μg in each lane), and resulting filters was hybridized with $^{32}$P-labeled probes to the PKA subunits RLα, RIIα, Cα and Cβ. The migration of 28S and 18S rRNAs are indicated by arrowheads. Signal intensity was evaluated by densitometric scanning of suitably exposed autoradiograms and corrected for differences in loading by densitometric scanning of photographs of ethidium bromide stained gels prior to transfer. (B) Immunoblot analyses of PKA subunits. Examination of CD3+ T cells from 2 normal blood donors (lanes 1 and 2), 2 individual HIV-infected patients with asymptomatic HIV infection (lanes 3 and 4) and 3 patients with symptomatic HIV infection (lanes 5, 6 and 7). Arrowheads indicate the migration of purified recombinant standards for PKA subunits. Equal loading was verified by densitometric scanning of Coomassie stained gels. Densitometric analyses of immunoblots indicated no (RIα, C) or minor (RIIα, 15% decrease, lanes 1 and 2 vs. lanes 5 to 7) differences in protein levels of patient samples versus controls.

FIG. 3. Inhibition of TCR/CD3 stimulated T cell proliferation by the cAMP agonist Sp-8-Bromo-cAMP-phosphorothioate (Sp-8-Br-cAMPS) and reversal of inhibition by the complementary cAMP antagonist Rp-8-Bromo-cAMP-phosphorothioate (Rp-8-BrcAMPS), was assessed in normal healthy blood donors (A) and HIV-infected patients (C). The effect of increasing doses of cAMP antagonist on TCR/CD3 stimulated proliferation of CD3+ T cells isolated from normal blood donors (13) and HIV patients (D) was examined separately in the same experiments. (A) and (B) show proliferation of CD3+ T cells from 3 healthy blood donors that were pooled and purified. (Q and (D): Proliferation of T cells from one patient with symptomatic HIV infection. Mean values of triplicate determinations ±SD are shown. See table 1 for summarized patient data (n=18). Note: Scaling differs in upper versus lower panels.

FIG. 4. Endogenous cAMP levels in T lymphocytes from CVI patients and healthy controls. (A) cAMP levels in negatively selected T lymphocytes from 13 CVI patients and 10 healthy controls. Data are given as medians. Error bars represent $25^{th}$–$75^{th}$ percentiles. *P<0,05 versus controls. (B) The effect of increasing concentrations of the cAMP agonist 8-(4-chlorphenylthio)cAMP (8-CPT-cAMP) on anti-CD3 stimulated T lymphocyte proliferation in one representative CVI patient (solid circles) and one healthy control (open circles) are shown. The maximal proliferation was normalized to 100%. Curve fit analyses were performed using Sigma plot, and $IC_{50}$ values were calculated demonstrating markedly decreased values for T lymphocytes from the CVI patient compared to control (2,26 μM versus 4,66 μM). For statistics between the CVI group, and controls, sec Table II. Note: Left-shift of $IC_{50}$ (arrow) and altered curve slope (Hill coefficient).

FIG. 5. Modulation of T cell proliferation by cAMP agonist and antagonist. Inhibition of anti-CD3 stimulated proliferation of T lymphocyte by the cAMP agonist (SP-8-Br-cAMPS) and reversal of inhibition by its complementary PKA type I selective antagonist (Rp-8-Br-cAMPS) are shown in one healthy control (A) and one representative CVI patient (C). The effect of increasing concentrations of Rp-8-Br-cAMPS on anti-CD3 stimulated T lymphocyte proliferation was also examined separately, and the results from one healthy control and one representative CVI patient are shown in panel (B) and (D), respectively. Data are given as mean values for triplicate determination ±SD. For statistics between the CVI group and controls, see Table II.

FIG. 6. Effect of cAMP antagonist on the release of IL-2 from T cells. IL-2 levels in supernatants from anti-CD3 stimulated T lymphocytes after 20 h of culture with or without the addition of different concentrations of the selective PKA type I antagonist Rp-8-Br-cAMPS (Rp) are shown. Panel A: healthy control. Panel B: representative CVI patient. Data are given as mean values for triplicate determination ±SD. For statistics between the CVI group and controls, see Table 4. * P<0,0 1 versus IL-2 level without antagonist. ** P<0,001 versus IL-2 level without antagonist.

Figure 7A:
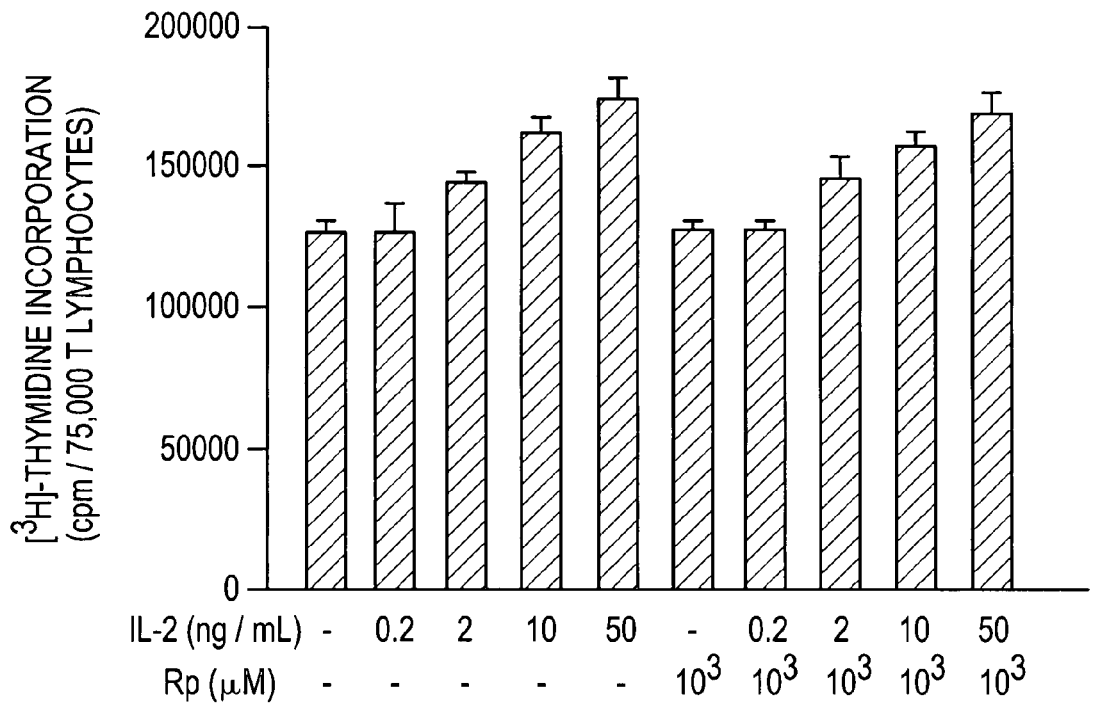
Figure 7B:
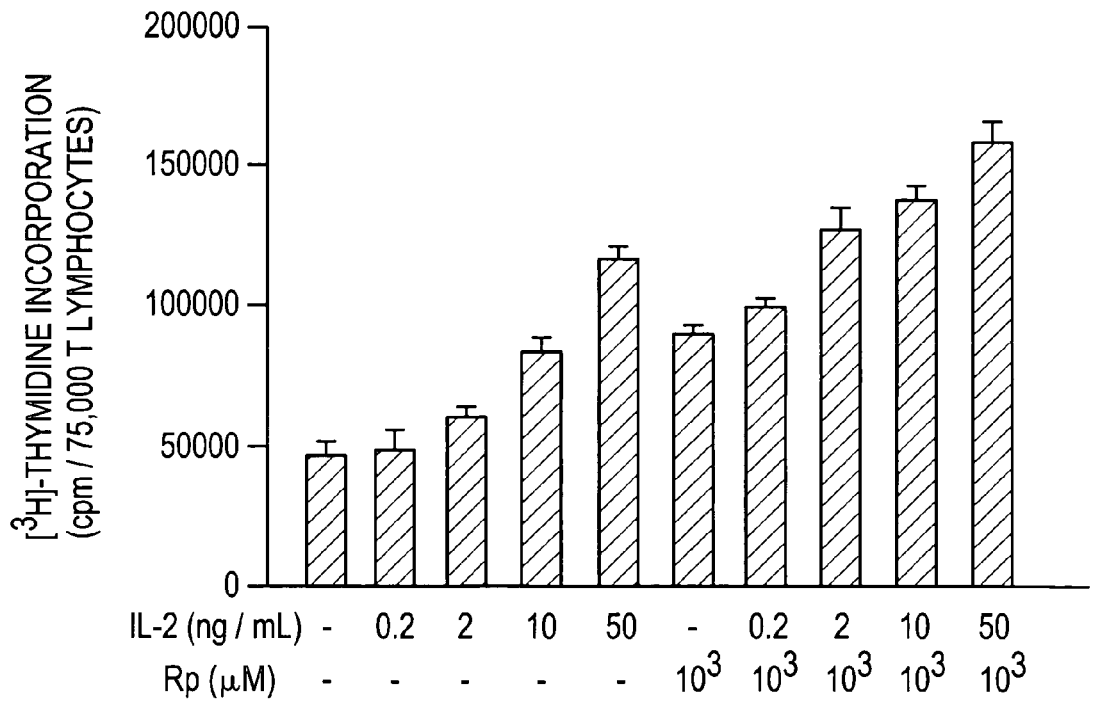

FIG. 7. Modulation of T cell proliferation by IL-2 and cAMP antagonist. The effect of increasing concentrations of IL-2 (2 Units/ng) with or without 1000 μM of Rp-8-Br-cAMPS (Rp) on anti-CD3 stimulated T lymphocyte proliferation are shown for one healthy control (A) and one representative CVI patient (13). Data are given as mean values for triplicate determination ±SD.

Figure 8:
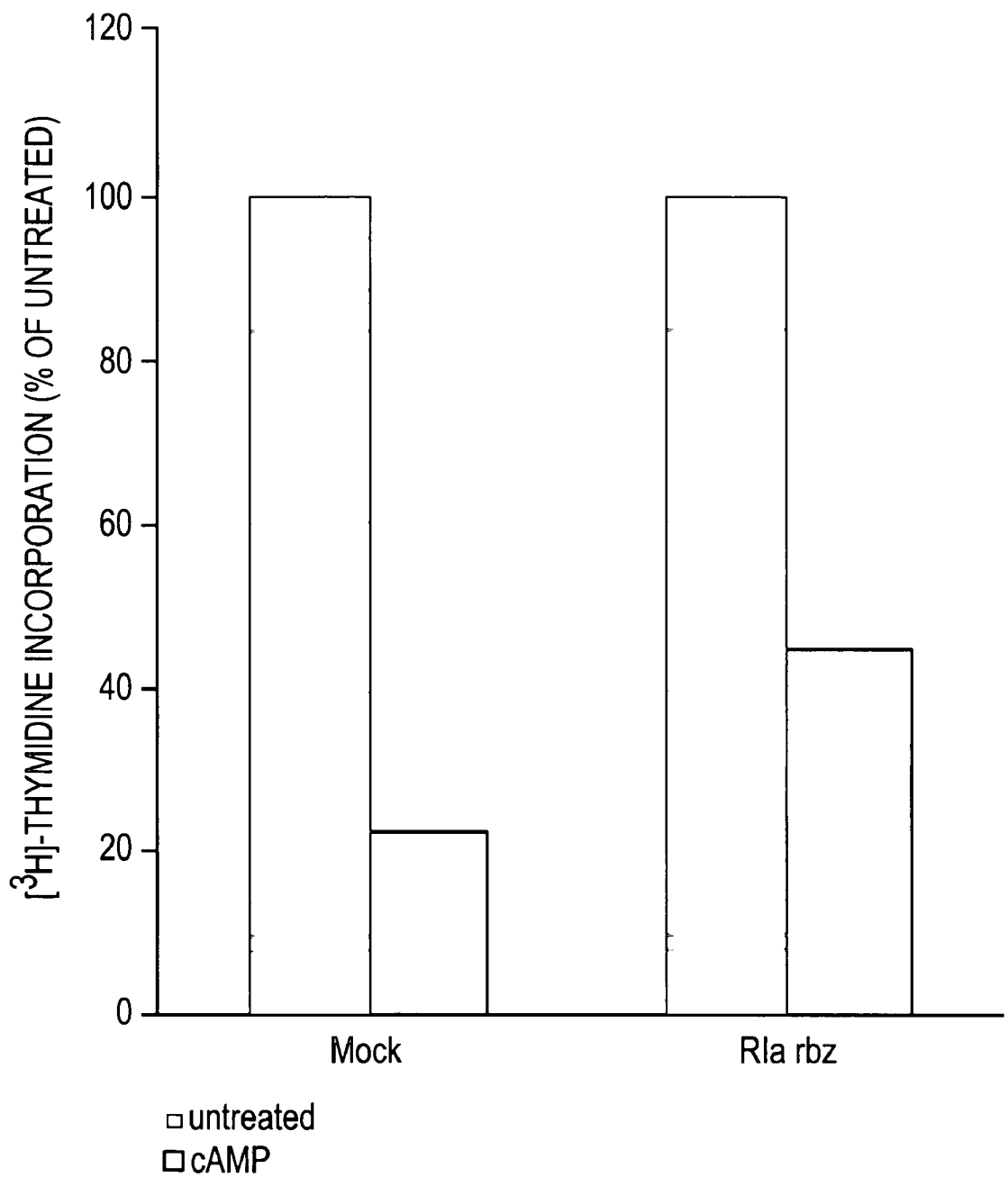

FIG. 8. Reversal of cAMP-mediated inhibition of TUR/CD3 stimulated T cell proliferation by the use of ribozyme to the RIα subunit of protein kinase A type I. TCR/CD3 stimulated proliferation of peripheral blood CD3+ T cells from normal healthy blood donor following treatment with liposomes alone (mock) or with liposomes and RIα ribozyme (RIα rbz, 10 μM) in the absence (solid bars) and presence (open bars) of 8-CPT-cAMP (12,5 μM).

Figure 9:
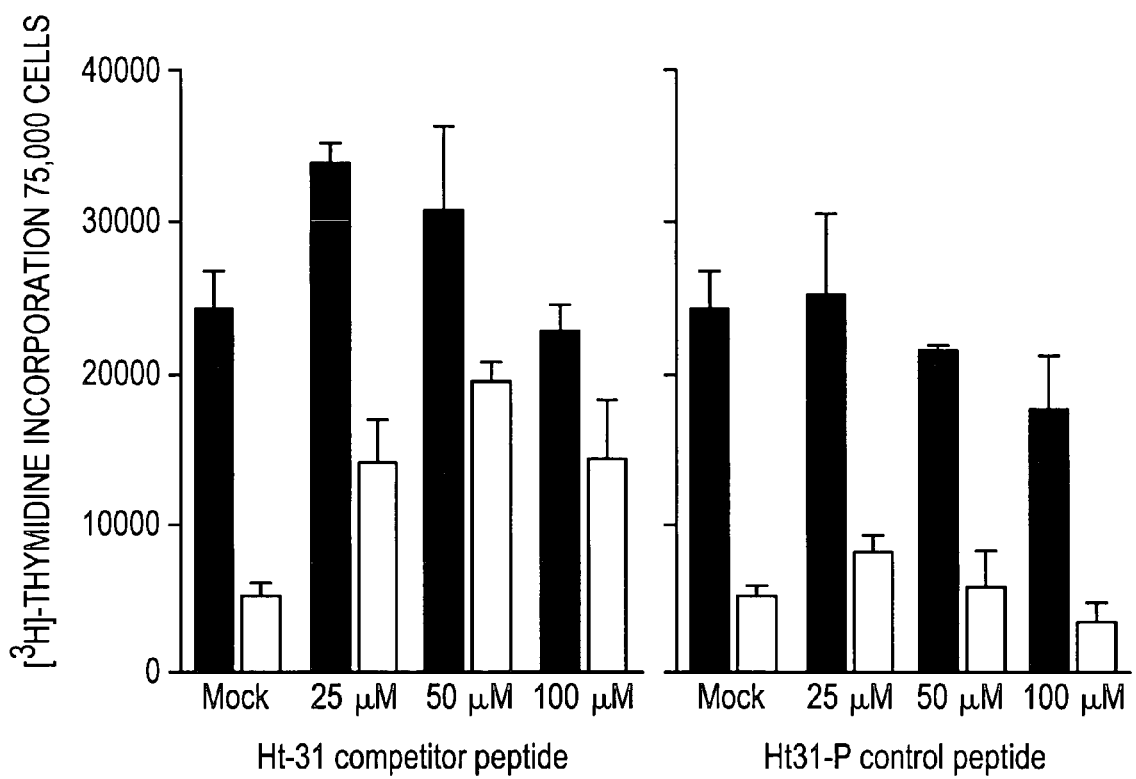

FIG. 9. Reversal of cAMP-mediated inhibition of TCR/CD3 stimulated T cell proliferation by the use of competitor peptide to compete the TCR/CD3 associated anchoring of RIα subunit of protein kinase A type I in T cells. TCR/CD3 stimulated proliferation of peripheral blood CD3+ T cells from normal healthy blood donor following treatment with liposomes alone (mock) or with increasing concentrations (25 to 100 μM) of a competitor peptide (Ht-31) that competes anchoring, to PKA type II or a control peptide (Ht31-P). Note: reduced sensitivity to cAMP following transfection with increasing concentrations of Ht31 competitor peptide, but not with the control peptide (Ht-31P).

FIG. 10. TCR/CD3 stimulated proliferation of peripheral blood CD3+ T cells in the presence of increasing, concentrations of 8-CPT-cAMP. Normalized levels of proliferation of T cells mock transfected with liposomes only (solid circles, continuous line) or incubated with liposomes and Ht31 peptide (35 μM) to compete anchoring of protein kinase A type I (open circles, dotted line) was assessed as [$^3$H]-thymidine incorporation after 48 h during which [$^3$H]-thymidine was added for the last 18 h. Note: right shift of the $IC_{50}$ (arrow) from 1,8 to 4,8 μM in the presence of 8-CPT-cAMP.

EXAMPLES

The following methods are used in the Examples:

Human peripheral blood CD3+ T cells were purified by negative selection from 50 ml of heparin-treated blood from normal healthy donors (Ullevaal University Hospital Blood Center, Oslo. Norway) or patients. Briefly, peripheral blood mononuclear cells were isolated by density gradient (Lymphoprep, NycoMed, Oslo, Norway) centrifugation followed by negative selection using monodisperse magnetic beads directly coated with antibodies to CD14 and CD19 and rat anti-mouse IgG beads coated with antibodies to CD56 and a magnet. Magnetic beads were all from Dynal (Oslo, Norway, cat. no. 111.12, 111.04, and 110.11. respectively) whereas anti-CD56 antibody was from Pharmingen (San Diego, Calif., cat. no. 31660.d). All steps were performed at 4° C. Cell suspensions were routinely screened by flow cytometry using fluorescent antibodies and a FacScan (Becton-Dickinson, San Diego, Calif.) and shown to consist of more than 90% CD3+ and low levels of CD 14+ (<2%), CD19+ (<2%) and CD56+ (<5%) cells.

Negative Selection of Peripheral Blood CD3+ T Cells

Peripheral blood CD3+ T cells were purified by negative selection from 50 ml of heparin-treated blood from normal healthy donors (Ullevaal University Hospital Blood Center, Oslo, Norway) or patients. Briefly, peripheral blood mononuclear cells were isolated by density gradient (Lymphoprep, NycoMed, Oslo, Norway) centrifugation followed by negative selection using, monodisperse magnetic beads directly coated with antibodies to CD14 and CD19 and rat anti-mouse IgG beads coated with antibodies to CD56 and a magnet. Magnetic beads were all from Dynal (Oslo, Norway, cat. no. 111.12, 111.04, and 110.11, respectively) whereas anti-CD56 antibody was from Pharmingen (San Diego, Calif., eat. no. 31660.d). All steps were performed at 4° C. Cell suspensions were routinely screened by flow cytometry and shown to consist of more than 90% CD3+ and low levels of CD14+ (<2%), Cl9+ (<2%) and CD56+ (<5%) cells.

Cyclic AMP Quantitation

Levels of endogenous cAMP were examined in peripheral blood CD3+ T cells. CD3+ T cells were isolated at 4° C. by negative selection and triplicate samples ($2\times10^6$ cells) were harvested, followed by subsequent extraction of cAMP and analysis of intracellular cAMP content as described elsewhere (8). Basal levels of cAMP were shown to be stable at 4° C. both in crude peripheral blood mononuclear cells and CD3+ T cells for more than 120 min (the interval required for purification of CD3+ T cells, data not shown).

Proliferation Assays

Proliferation assays were performed by incubation of $0.75\times10^6$ CM+ T cells/ml in a 100 μl volume in that-bottom 96-well microtiter plates. Activation was achieved by subsequent addition of monodisperse magnetic beads coated with sheep anti-mouse IgG (Dynal. cat. no. 110.02) at a cell:bead ratio of 1:1 followed by addition of antiCD3 (clone $SpvT_3b$) at a final dilution of 1:125,000 for the experiments shown. The optimal concentration of antibody was titrated carefully in the initial setup and parallel experiments at several different dilutions of antibody was always performed. Proliferation was analyzed by incubating, cells for 72 hours during which [$^3$H]thymidine was included for the last 16 hours. Cells were washed and harvested onto filters using a Scatron harvester (Suffolk, UK) and subsequently analyzed by β-scintillation counting. cAMP analogs, when used, were added 30 min prior to activation by addition of anti-CD33 antibodies. 8-CPT-cAMP was from Sigorna (St. Louis, Mo.) and Sp- and Rp-8-Br-cAMPS were from BioLog Life Science Company (Bremen, Germany) and were all dissolved to concentrations of 4 to 10 mM in PBS and concentrations calculated using the extinction coefficients given by the manufacturer.

Determination of IL-2 Levels.

For determination of IL-2 levels and IL-2 receptor binding, negatively selected CD3 lymphocytes ($10^6$/ml, 200 µL/well) were cultured in medium alone or stimulated with anti-CD3 (clone SpvT$_3$b) with or without preincubation with different concentrations of Rp-8-Br-cAMPS. The anti-CD3 antibodies were either cross-linked with immunomagnetic beads (IL-2 levels; final anti-CD-3 dilution 1:125000) or precoated on the wells (IL-2 receptor binding; final dilution 1:1500). After 20 h of culture, cellfree supernatants were harvested and stored at −80° C. until analysis. The IL-2 levels in supernatants were determined by an ELISA (R&R Systems, Minneapolis, Minn.).

Determination of Prostaglandin $E_2$ (PGE,) Levels in Monocyte Supernatants

Stimulated (LPS from *Escherichia coli* 026B6: final concentration 10 ng/n-LL; Sigma) and unstimulated cells (3×105 monocytes/mL, 200 µL/well) were cultured in RPMI 1640 (Gibeo) with 2 mmol/L L-glutamine supplemented with 10% human AB serum or in serum-free medium (X-Vivo 15; Bio Whittaker, Inc.). Cell-free supernatants were harvested after 24 h, and $PGE_2$ concentration was determined by ELISA (Cayman Chemical, Ann Arbor, Mich.).

Miscellaneous.

If not noted standard methods known the person with knowledge in the art are used.

Example 1

Cyclic AMP completely abolishes T cell proliferation induced through the T cell receptor/CD3-complex (TCR/CD3) as well as early tyrosine phosphorylation following engagement of the antigen receptor (1, 2). We have previously shown that activation of cAMP-dependent protein kinase (PKA) type I is necessary and sufficient to mediate the inhibitory effect of cAMP on T cell signaling, and that PKA type I redistributes to and colocalizes with the antigen receptor during activation and capping of T cells (2, 3). This serves to establish PKA type I as an acute negative modulator of T cell antigen responses and clonal expansion. T cell dysfunction is an early event in the course of HIV-infection and a major factor in the development of severe immunodeficiency. However, the molecular mechanisms by which HIV impairs T cell function have not been revealed. Two recent publications provide indications that HIV-derived peptides may increase cAMP levels in vitro (4, 5). Furthermore, cAMP treatment increased HIV reverse transcriptase activity 5 to 10-fold in a cultured T cell line (6). Together this may serve to establish a circulus vitiosus in the HIV-infected T cell. However, any link between the cAMP signaling pathway and the HIV-induced T cell dysfunction has not yet been established. For this reason, we investigated the possible role of cAMP mediated inhibition of T cell immune function in purified T cells from HIV-infected patients prior to and during highly active antiretroviral therapy. We demonstrate that increased activation of PKA type I significantly inhibits T cell proliferation in cells from HIV-infected individuals independent of ongoing potent antiretroviral therapy and that this effect can be reversed by a specific antagonist of PKA type 1.

Results

Elevated Levels of cAMP in T Cells from HIV-Infected Individuals

In negatively selected, highly purified T cells from nine consecutive HIV-infected patients (independent of clinical status) the endogenous levels of cAMP were significantly elevated compared to the levels in CM+ T cells concomitantly isolated from 10 HIV seronegative blood donors (1238 vs. 688 fmol, $10^6$ cells, p<0.05, see FIG. 1A). Furthermore, the effect of cAMP agonist on TCR/CD3-induced proliferation was investigated in 18 individual HIV-infected patients not receiving, any potent antiretroviral therapy with HIV protease inhibitor and 8 seronegative controls (Tables 1 and 2a). The patients were classified in two groups, one group with asymptomatic and the other with symptomatic HIV infection (AIDS and non-AIDS) (Table 1), according, to (7). T cells from HIV-infected patients revealed a highly significant increase in sensitivity to inhibition of cell proliferation by exogenously added 8-CPT-cAMP (FIG. 1B and Table 1 and 2a, p<0.001, n=18). Moreover, when the maximal proliferation rates of T cells from HIV-infected patients and that of seronegative T cells were normalized to 100% (FIG. 1B and data not shown), it was evident that in addition to a distinct left-shifted cAMP-inhibition curve, the slopes of the curves were significantly different (Hill coefficients of 1.19 (1.13–1.40) for T cells from HIV seropositive individuals versus 1.59 (1.40–1.81) for normal T cells, Table 1, p<0.01, n=18). The increased sensitivity to inhibition by cAMP analog suggests a contribution from elevated endogenous cAMP in priming cAMP binding site B of PKA type I with subsequent increase in the affinity of the A site for the exogenously added cAMP analog. The shift in curve slope from a cooperative, two-ligand site binding, situation to an apparent non-cooperative inhibition curve by 8-CPT-cAMP also indicates B-site occupancy by endogenous cAMP.

Unchanged Levels of PKA Type I in CD3+ T Cells from HIV-Infected Patients

We next examined the levels of PKA subunits in HIV-infected patients compared to normal blood donors. FIG. 2A shows mRNA levels of PKA subunits in total RNA extracted from 3 blood donors (lane 1) and total RNA extracted from CD3+ cells from 10 patients with symptomatic HIV infection. No changes were seen in mRNA levels of RIα and Cβ in HIV infected patients compared to normal blood donors. Whereas a slight increase (20%) was seen in mRNA for RIIa in patients with symptomatic HIV infection, a 20% decrease was seen in Cα mRNA levels. Immunoblot analyses (FIG. 2B) further demonstrated that the levels of RIa protein (upper panel) were unchanged in asymptomatie patients (lane 3 and 4) as well as in symptomatic patients (lane 5, 6 and 7) when compared to 2 normal blood donors (lane 1 and 2). Protein levels for RIIa (middle panel) revealed very minor changes (15% decrease) in patients with symptomatic HIV infection compared to normal controls as evaluated by densitometric scanning. Levels of C subunit were unchanged as detected by an antibody reactive with both Cα and Cβ (lower panel). Thus, levels of PKA I constituted by RIα and Cα or Cβ, appeared unchanged and only very moderate changes were seen in the levels of PKA II (constituted by RIIα and C) in HIV infected patients.

PKA Type I Antagonist Improves T Cell Proliferation of T Cells from HIV-Infected Patients In order to further assess the specificity of the inhibition of TCR/CD3-induced T cell proliferation, we used a sulfur-substituted cAMP analog (Rp-8-Br-cAMPS) working as a full antagonist for PKA type 1 (8). FIG. 3A shows that in T cells from normal blood donors, TCR/CD3-stimulated proliferation was inhibited by a cAMP agonist (Sp-8-Br cAMPS). This effect was almost completely reversed by increasing concentrations of complementary antagonist (Rp-8-Br-cAMPS). However, antagonist alone did not alter proliferation of normal T cells (FIG. 3B). In contrast, when the TCR/CD3-induced proliferation of T cells from a HIV-infected patient was investigated, we observed that not only did the use of the antagonist (Rp-8-Br-cAIWPS) reverse the effect of the complementary agonist, but further increased the proliferation above the levels in untreated cells (FIG. 3C). When the effect of the cAMP antagonist alone was assessed in T cells from HIV-infected patients, we observed a concentration-dependent increase in TCR/CD3-induced proliferation that was more than 2-fold at higher concentrations (FIG. 3D). The degree of increased proliferation following, treatment with cAMP antagonist was inversely correlated with the level of TCR/CD3-induced proliferation in the absence of antagonist ($p<0.001$, $R=0.78$, $n=18$. Table 1), i.e. T cells responding, poorly to TCR/CD3 stimulation benefited most from cAMP antagonist treatment. The stimulatory effect of the cAMP antagonist was not saturated even at the highest concentrations used (FIG. 3D; similar data (not shown) were obtained for all patients in Table 2). This indicates that the solubility of the compound, affinity, or availability to cells may be a limiting factor for the effect observed. Thus, a more permeable and potent PKA type I antagonist, when available, may further improve TCR/CD3-induced proliferation of T cells from HIV-infected patients.

Patients on Highly Active Antiretroviral Therapy Have a Persistent T Cell Dysfunction that can be Improved with PKA Type I Antagonist Recently, HIV protease inhibitors have been found to slow the progression HIV-1 disease and to strongly reduce levels of plasma HIV RNA (9, 10). For this reason, we next examined T cell proliferation, cAMP sensitivity and the effect of cAMP antagonist on T cells from 9 symptomatic HIV-infected patients receiving potent antiretroviral treatment with the HIV protease inhibitor indinavir in combination with nucleoside analogs. TCR/CD3-induced proliferative response was increased compared to untreated patients with symptomatic HIV-infection who did not receive protease inhibitor ($p<0.05$; Table 1, lower part and Table 2b). However, immune response of T cells from treated patients was still significantly reduced compared to normal controls ($p<0.001$) indicating that the HIV-specific T cell dysfunction persists despite of potent antiretroviral treatment. Furthermore, sensitivity to inhibition by cAMP was still significantly increased compared to normal controls ($p<0.01$), and incubation of T cells from patients on highly active antiretroviral therapy with cAMP antagonist significantly improved TCR/CD3-induced T cell proliferation compared to that of T cells from normal individuals ($p<0.05$). In addition, single patient data from this group revealed heterogeneity among the patients receiving potent antiretroviral therapy (Table 2b). Proliferation of T cells from 6 of 9 patients benefited from Rp-8-BrcAMPS in a dose-dependent manner (1.5 to 2.8-fold increase in immune response) whereas T cells from 3 patients with subnormal proliferative response did not respond to cAMP antagonist (proliferation 0.98 to 1.11-fold of that in untreated cells). This is reflected in the inverse correlation of the level of TCR/CD3-induced proliferation in the absence of antagonist and the effect of treatment with the cAMP antagonist ($p<0.01$, $R=0.81$, $n=9$); i.e. only T cells from patients with persistent T cell dysfunction benefited from treatment with cAMP antagonist. A follow-up of 4 of the 18 untreated patients examined in Table 1 and 2a after initiation of highly active antiretroviral therapy, showed increased proliferative response of T cells after onset of treatment (compare Table 2a and 2b). However, T cells from 2 of the patients remained severely suppressed in immune response (labeled a and b), and T cell proliferation from these patients still benefited substantially from incubation with cAIVIP antagonist. Cells from the two other patients (labeled c and d) reached subnormal levels of T cell proliferation after onset of potent antiretroviral therapy and did not benefit further from incubation with Rp-8-Br-cAMPS.

TABLE I

Summarized data for normal controls, patients classified into groups with asymptomatic and symptomatic HIV-infection according to (7), and syptomatic patients on highly active antiretroviral therapy.

| Clinical status | CD4+lympocyte count Cells/μL | HIV-RNA Copies/ml plasma | α-CD3-induced proliferation [³H]-thymidine incorporation (cpm) | Inhibition of proliferation by 8-CPT-cAMP $IC_{50}(\mu M)^+$ | Inhibition of proliferation by 8-CPT-cAMP Hill coefficient | Increase in proliferation by Rp-8-Br-Camps Fold increase compared to untreated |
|---|---|---|---|---|---|---|
| Normal, n = 8 | 660(520–980)[p] | n.d. | 132484(121181–138453) | 4.59(4.04–5.82) | 1.59(1.40–1.81) | 1.01(0.93–1.14) |
| HIV+ asymptomatic, n = 8 | 154(115–203) | 7850(200–48400) | 54558(35995–77164)[w] | 2.26(1.96–2.64)[b] | 1.18(1.09–1.36)[b] | 1.50(1.29–1.73)[b] |
| HIV+ symptomatic, n = 10 | 42(10–112) | 69300(13700–333300) | 26817(16745–40035)[w] | 1.87(1.69–2.30)[w] | 1.19(1.13–1.40)[o] | 1.62(1.48–2.00)[w] |
| Triple combination therapy, n = 9 | 325(220–340) | 0(0–2070) | 70679(32768–76695)[w] | 2.59(1.86–3.73)[b] | 1.35(1.33–1.68) | 1.53(1.11–1.77)[o] |

TABLE I-continued

Summarized data for normal controls, patients classified into groups with asymptomatic and symptomatic HIV-infection according to (7), and syptomatic patients on highly active antiretroviral therapy.

| Clinical status | CD4+lympocyte count Cells/μL | HIV-RNA Copies/ml plasma | α-CD3-induced proliferation [³H]-thymidine incorporation (cpm) | Inhibition of proliferation by 8-CPT-cAMP IC$_{50}$(μM)$^+$ | Inhibition of proliferation by 8-CPT-cAMP Hill coefficient | Increase in proliferation by Rp-8-Br-Camps Fold increase compared to untreated |
|---|---|---|---|---|---|---|

Data are presented as median values and a 25 to 75% range is indicated in parenthesis. $^+$IC$_{50}$ denotes the concentration of cAMP analog necessary to produce a half-maximal inhibition of CD3-induced T cell proliferation. $^P$Range of CD4+ lymphocyte count in 21 blood donors. n.d.: not done. Anti-CD3-induced T cell proliferation, inhibition of proliferation by 8-CPT-cAMP (IC$_{50}$ and Hill coefficient) and increase in proliferation following treatment with Rp-8-Br-cAMPS in normal versus HIV-infected CD3+ T cells were analyzed by Mann-Whitney U test. Significance: $^o$denotes p < 0.05, $^b$denotes p < 0.01 and $^w$denotes p < 0.001. Triple combination therapy denotes patients with HIV-infection receiving highly active antiretroviral therapy with a combination of HIV protease inhibitor (indinavir) and nucleoside analogs zidovudine and lamivudine.

TABLE 2a

Individual patient data.

| Patients* | Clinical statusH | αCD3-induced proliferation [3H]-thymidine incorporation (cpm) | Inhibition of proliferation by 8-CPT-cAMP IC50 (mM) | Increase in proliferation by Rp-8-Br-cAMPS Fold increase compared to untreated |
|---|---|---|---|---|
| #1$^a$ | s | 11838 | 0.9 | 2.81 |
| #2$^b$ | s | 13150 | 1.87 | 2.02 |
| #3 | s | 16745 | 1.57 | 2.73 |
| #4 | s | 17981 | 1.82 | 1.48 |
| #5 | s | 21430 | 1.69 | 1.77 |
| #6 | a | 29957 | 2.15 | 1.96 |
| #7 | s | 32203 | 3.13 | 1.5 |
| #8$^c$ | a | 33887 | 2.63 | 1.79 |
| #9 | s | 34857 | n.d. | 1.74 |
| #10 | a | 38102 | 1.78 | 1.3 |
| #11 | s | 40035 | 2.36 | 1.49 |
| #12$^d$ | s | 45686 | 2.28 | 1.43 |
| #13 | s | 50051 | 2.03 | 1.46 |
| #14 | a | 52195 | 2.14 | 1.67 |
| #15 | a | 56920 | 2.36 | 1.6 |
| #16 | a | 62248 | 4.04 | 1.27 |
| #17 | a | 92080 | 2.66 | 1.39 |
| #18 | a | 98644 | 1.55 | 1.16 |

*Patients were ordered according to α-CD3-induced proliferative response.
n.d.: not done.
HClinical status: a: asymptomatic HIV-infection, s: symptomatic HIV-infection (AIDS or non-AIDS).
$^{a,b,c,d}$denotes single patients followed up during highly active antiretroviral therapy.

TABLE 2b

Data from individual patients receiving highly active antiretroviral therapy.

| Patients* | aCD3-induced proliferation [3H]-thymidine incorporation (cpm) | Inhibition of proliferation by 8-CPT-cAMP IC50 (mM) | Increase in proliferation by Rp-8-Br-cAMPS Fold increase compared to untreated |
|---|---|---|---|
| #1$^a$ | 15137 | 1.31 | 2.79 |
| #2 | 24173 | 2.24 | 2.65 |
| #3$^b$ | 32768 | 1.1 | 1.77 |
| #4 | 63523 | 3.83 | 1.53 |
| #5$^c$ | 70679 | 2.69 | 1.04 |
| #6 | 75380 | 1.86 | 1.77 |
| #7 | 76695 | 2.59 | 1.52 |
| #8 | 85138 | 3.73 | 0.98 |
| #9$^d$ | 92199 | 5.31 | 1.11 |

*Patients were ordered according to α-CD3-induced proliferative response. Treatment was with indinavir, lamivudine and zidovudine.
$^{a,b,c,d}$denotes patients where data prior to initiation of highly active antiretroviral therapy are available (compare Table 2a).

Example 2

The present study demonstrates for the first time increased endogenous cAMP levels in T cells from CVI patients, and even more importantly, that a selective inhibition of PKAT could markedly improve or in some cases even fully restore anti-CD3-induced T cell proliferation in CVI patients with impaired T cell function. These findings indicate a possible intracellular mechanism for the T cell defect in CVI and suggest that the cAMP/PKAI system may be a potential target for immunomodulating therapy in these patients.

The Effect of cAMP Antagonist on PBMC Proliferation

In order to address the possible role of the cAMP/PKAI system in the impaired T cell function in CVI, we first examined whether a sulfur-substituted cAMP analog (Rp-8Br-cAMPS), working as a full antagonist for PKAI (8), could improve anti-CD3 stimulated proliferation of PBMC in 20 CVI patients and 15 healthy controls. Confirming previous results (12,11), stimulated lymphocyte proliferation was significantly impaired in this CVI population compared with control subjects (data not shown). Furthermore, while antagonist did not significantly alter proliferation of lymphocytes obtained from normal blood donors (Panel A), Rp-8-Br-cAMPS induced a significant and concentration-dependent improvement of anti-CD3 stimulated proliferation in the CVI group (data not shown). However, single patient data from the CVI group revealed heterogeneity. Whereas more than 100% increase in anti-CD3 induced lymphocyte proliferation was found in 7 of the CVI patients, 5 of the patients had less than 40% increase in proliferation when the cAMP antagonist was added to cells in vitro. Of note, the patients with the most marked increase in lymphocyte proliferation by cAMP antagonist, were those with the most severely depressed proliferative response after anti-CD3 stimulation (r=−0.85; P<0.001).

The Effect of cAMP Agonist and Antagonist in Purified T Lymphocytes

Figure 4A:
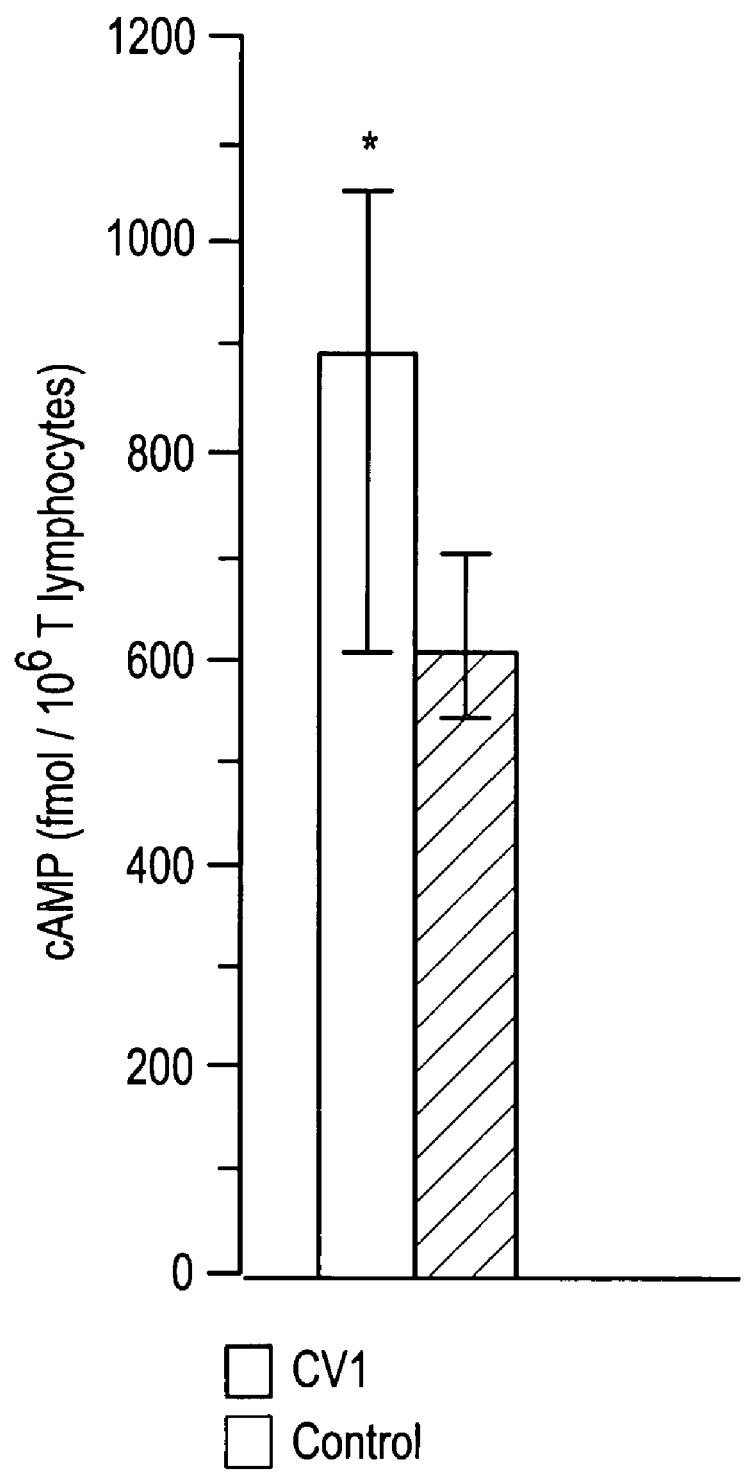
Figure 4B:
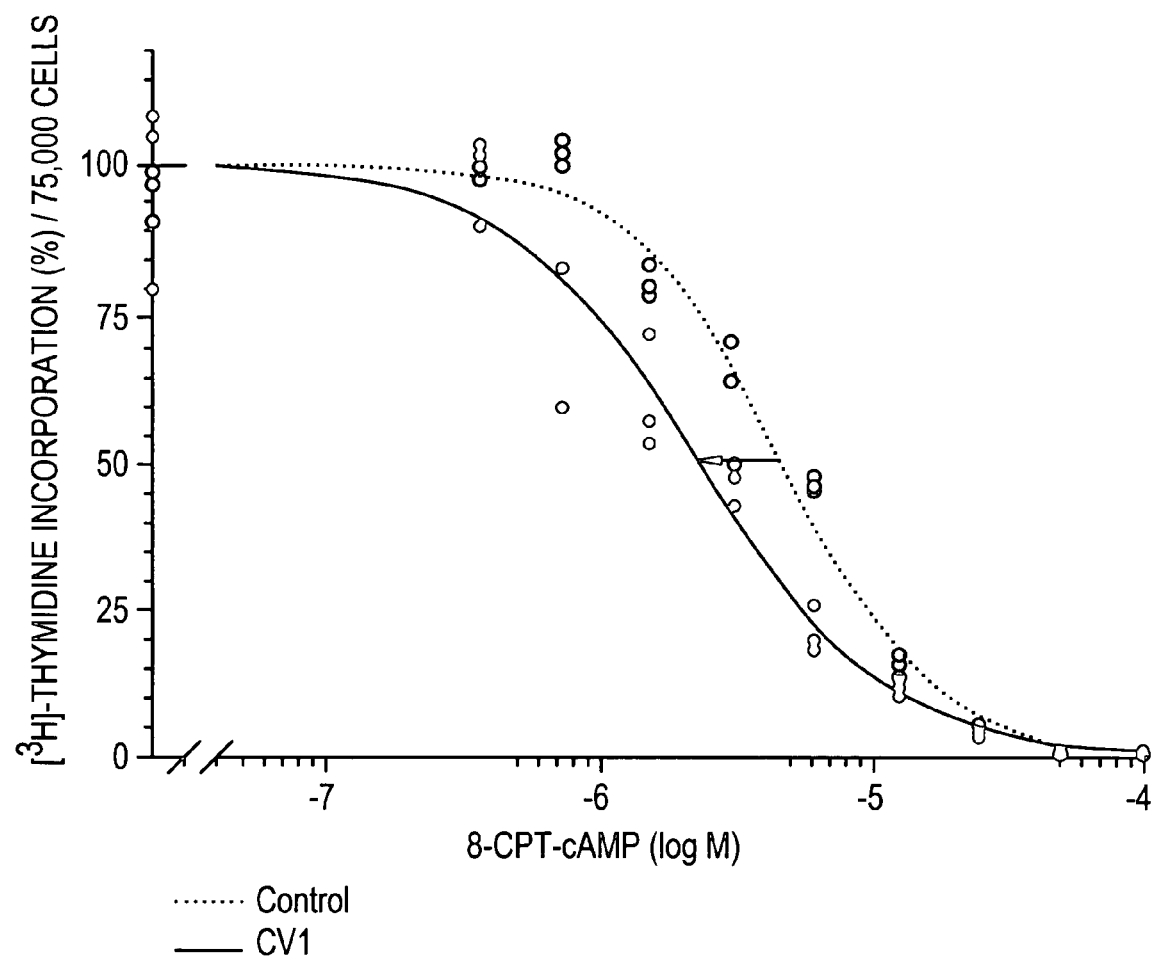

To better study the role of the cAMP/PKAI system in the induction of T cell dysfunction in CVI, we analysed the endogenous cAMP levels and the effects of cAMP agonist and antagonist on proliferation in negatively selected, purified T lymphocytes. We first measured cAMP levels in T lymphocytes from 13 of the CVI patients and 10 healthy controls, and found significantly higher cANT levels in the CVI group (FIG. 4A). The sensitivity to cAMP-dependent inhibition of T cell proliferation was also increased showing the positive cooperative effect of endogenous cAMP levels (FIG. 4B). The results presented in Table 3 show such effect of 8-CPT/cAMP on cell proliferation in 7 separate CVI patients with markedly impaired antiCD-3 stimulated T cell proliferation, compared with the effect in 8 control subjects. This significant increase in sensitivity to inhibition of cell proliferation by exogenously added 8-CPT-cAMP in the CVI group was reflected in a marked decrease in $IC_{50}$ values in these patients, primarily due to a change in the slope for the inhibition curve (Hill coefficient; Table 3 and FIG. 4B).

To further address the specificity of the inhibition of anti-CD3 stimulated T cell proliferation we used a cAMP agonist (Sp-8-Br-cAMPS) and its complementary PKAI selective antagonist (Rp-8-Br-cAMPS). In healthy controls the inhibitory effect of the cAMP agonist was completely reversed by its complementary antagonist (FIG. 5A), but the antagonist alone did not further enhance T cell proliferation (FIG. 5B and Table 3). In contrast, we found a concentration-dependent increase in anti-CD3 stimulated proliferation in CVI patients (>100% increase in 3 patients and reaching level within normal range in 2 patients) when Rp-8-Br-cAMPS was added to cell cultures (FIGS. 5C and D and Table 3). Thus, it seems that in CVI patients, T lymphocytes with impaired anti-CD3 stimulated proliferation are characterized by chronically elevated endogenous cAMP levels, and treatment with a selective PKAI antagonist markedly improves anti-CD3 stimulated proliferation in these cells, reaching proliferation levels comparable to healthy controls (~25% and 75% of levels in healthy controls, with and without Rp-8-Br-cAMPS, respectively).

The Effect of cAMP Antagonist on Proliferation of $CD4^+$ and $CD8^+$ Lymphocytes We next, by flow cytometry analysis of BrdU incorporation, examined anti-CD3 stimulated T lymphocyte DNA synthesis in the presence and absence of Rp-8-Br-cAMPS in subsets of $CD4^+$ and $CD8^+$ T lymphocytes in 8 CVI patients with impaired lymphocyte function and 7 controls. In CVI patients there was a significant increase in percent of $BrdU^+$ $CD4^+$ T lymphocytes when cAMP antagonist was added to cell culture [55.8 (40.7–77.0)% versus 69.6 (50.5–90.0)%, without and with antagonist, respectively, P<0.03]. In most patients the maximal increase was found at the highest concentration of Rp-8-Br-cAMPS (1000 µM). No effect of Rp-8-Br-cAMPS on DNA synthesis was seen in $CD4^+$ lymphocytes from healthy controls (data not shown). For $CD8^+$ lymphocytes there was no significant increase in percent of $BrdU^+$ cells after addition of cAMP antagonist in neither CVI patients nor controls, although a modest increase was seen in three CVI patients (data not shown).

The Effect of cAMP Antagonist on IL-2 Levels and IL-2 Receptor Binding in T Lymphocytes IL-2 plays a pivotal role in the growth and function of T lymphocytes (13), and decreased IL-2 production from these cells may play an important role in the immunopathogenesis of CVI (14,15). Cyclic AMP decreases IL-2 production and IL-2 receptor expression in T lymphocytes (16,17). To further elucidate the mechanism(s) of cAMP-induced inhibition of T lymphocyte proliferation in CVI, we therefore examined the effect of Rp-8-Br-cAMPS on IL-2 levels in supenatants from anti-CD') stimulated T lymphocytes in 7 CVI patients with impaired lymphocyte function and 8 controls. Compared with control subjects, T lymphocytes from CVI patients released significantly lower IL-2 levels into supernatants (Table 4), and we found a marked and concentration-dependent increase in IL-2 levels in the presence of cAMP antagonist (Table 4 and FIG. 6B). The effect of Rp-8-Br-cAMPS on IL-2 levels of CVI T cells was largely similar to that on proliferation. However, in spite of the dramatic increase in IL-2 levels after addition of Rp-8-Br-cAMPS to cell cultures in CVI patients, the IL-2 levels were still markedly lower than that found in control subject (Table 4). Thus, in CVI patients T lymphocyte proliferation is normalized to a larger extent than IL-2 secretion by addition of cAMP antagonist to cells in vitro.

We next examined by flow cytometry if the addition of Rp-8-Br-cAMPS to cell cultures also could influence IL-2 receptor binding in anti-CI3 stimulated T cells from 8 CVI patients with impaired lymphocyte function and 6 controls. In anti-CD3 stimulated cells there was no significant difference in IL-2 receptor binding between CVI patients and controls, neither in $CD4^+$ nor $CD8^+$ lymphocytes. However, in $CD4^+$ lymphocytes from CVI patients, but not in $CD8^+$ lymphocytes, there was a moderate but significant increase in IL-2 receptor binding after addition of Rp-8-Br-cAMPS to cell culture. No such increase was found in cells from healthy controls.

The Effect of Exogenously Added IL-2 in Combination with cAMP Antagonist on Anti-CD3 Induced T Lymphocyte Proliferation.

Figure 6B:
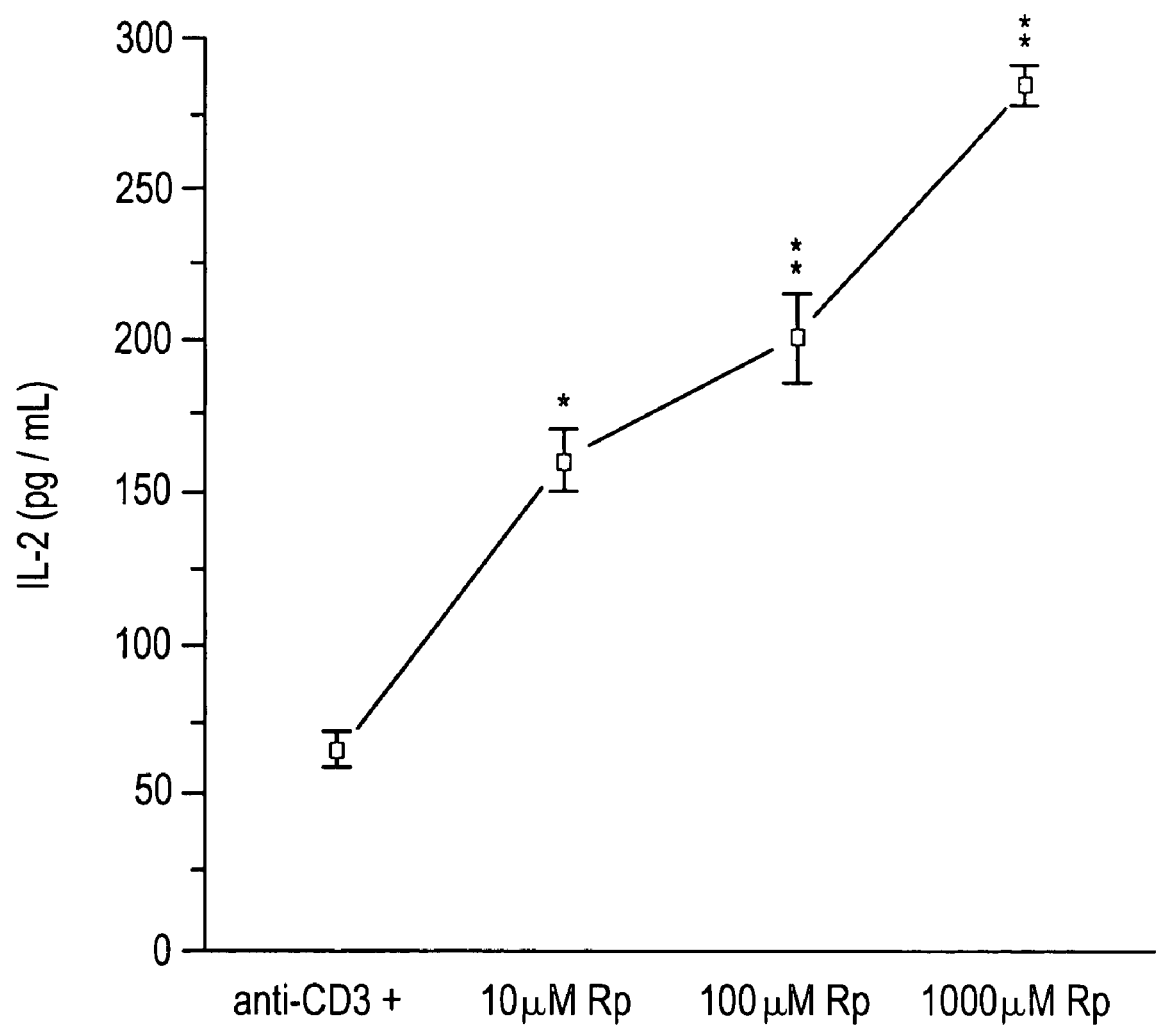

To further examine the role of IL-2 in the enhancement of T cell proliferation by addition of cAMP antagonist, we examined the effect of exogenously added IL-2 either alone or in combination with Rp-8-Br-cAMPS on anti-CD3 stimulated T cell proliferation in 4 CVI patients with impaired lymphocyte proliferation and 4 controls. After addition of IL-2 to cell culture there was a marked increase in proliferation in both CVI patients and controls (FIG. 7). However, at IL-22 concentrations comparable to the achieved increase in IL-2 levels after addition of cAMP antagonist (~0.15 ng/mL. FIG. 6B), no significant effect was seen on proliferation in neither CVI patients nor controls (FIG. 7). In facts the enhancing effect of cAMP antagonist in CVI patients was comparable to the effect of 15 ng/mL IL-2 FIG. 7). In CVI patients the enhancing effects of Rp-8-Br-eAMPS and IL-2 on T lymphocyte proliferation were additive (FIG. 7).

TABLE 3

Effect pf cAMP antagonist and agonist on anti-CD3 stimulated T cell proliferation i 7 CV patients and 8 healthy controls.

| Patient | anti-CD3 stimulated proliferation (cpm) | Highest proliferation when adding Rp-8-Br-cAMPS (cpm) | Increase in proliferation by Rp-8-Br-cAMPS (fold increase) | Inhibition of proliferation by 8-CPT-cAMP ($IC_{50}$ μM)* | Inhibition of proliferation by 8-CPT-cAMP (−Hill coefficient) |
|---|---|---|---|---|---|
| #1[a] | 4.870 | 11.932 | 2.45 | 2.98 | 1.47 |
| #2[b] | 26.968 | 98.972 | 3.67 | 2.26 | 1.26 |
| #3 | 35.224 | 60.938 | 1.73 | 3.68 | 1.34 |
| #4[c] | 36.740 | 77.154 | 2.10 | 3.36 | 1.38 |
| #5[d] | 66.050 | 123.513 | 1.87 | 3.16 | 2.03 |
| #6[e] | 78.080 | 104.627 | 1.34 | 2.66 | 1.39 |
| #7 | 109.567 | 150.107 | 1.37 | 2.34 | 1.46 |
| median (25–75th percentiles in CVI) | 36.740[+] (26.968–78.080) | 98.1 (60.938–123.513) | 1.87[+] (1.37–2.45) | 2.98[+] (2.34–3.36) | 1.39[§] (1.34–1.47) |
| median (25–75th percentiles in controls) | 132.300 (117.033–139.733) | 129.530 (119.316–160.692) | 1.01 (0.93–1.14) | 4.59 (4.04–5.82) | 1.59 (1.40–1.81) |

The individual values for the actual variables are given in 7 CVI patients ordered according to anti-CD3 stimulated T cell proliferative response. The group values for the actual variables are given in the CVI and the control group as medians and 25th–75th percentiles.
*$IC_{50}$ denotes the concentration of cAMP analog necessary to produce a half-maximal inhibition of anti-CD3 stimulated T cell proliferation.
[+]P < 0.005, [§]P < 0.02 versus controls; versus controls [a,b,c,d,e]denotes single patients also evaluated for IL-2 release (see Table 4).

TABLE 4

Effect of cAMP antagonist (Rp-8-Br-cAMPS) on IL-2 levels in supernatants from anti-CD3 stimulated T lymphocytes in 7 CVI patients and 8 healthy controls

| Patient | anti-CD3 stimulated IL-2 release (pg/mL) | Highest IL-2 level when adding Rp-8-Br-cAMPS (pg/mL)* | Increase in IL-2 level by Rp-8-Br-cAMPS (fold increase)* |
|---|---|---|---|
| #1[b] | 32 | 144 | 4.50 |
| #2 | 65 | 284 | 4.37 |
| #3[d] | 79 | 210 | 2.66 |
| #4[e] | 100 | 249 | 2.49 |
| #5 | 112 | 262 | 2.34 |
| #6[c] | 130 | 246 | 1.89 |
| #7[a] | 131 | 232 | 1.77 |
| median (25–75th percentiles) in CVI | 100[+] (130–65) | 246[+] (210–262) | 2.50[+] (4.37–1.89) |
| median (25–75th percentiles in controls) | 600 (510–800) | 799 (510–968) | 1.28 (1.06–1.45) |

The individual values for the actual variables are given in 7 CVI patients ordered according to anti-CD3 stimulated IL-2 levels in T cell supernatants. The group values for the actual variables are given in CVI and control group as medians and 25th–75th percentiles.
*While all CVI patients had highest IL-2 levels when 1000 μM of Rp-8-Br-cAMPS was added to cell cultures, the most pronounced effect in controls was seen at a lower antagonist concentration (100 μM).
[+]P < 0.005, [§]P < 0.02 versus controls; [a,b,c,d,e]denotes single patients also evaluated for T cell proliferation (see Table 3).

Example 3

A ribozyme directed to the RIα subunit of protein kinase A was developed and shown to completely cleave RIα mRNA in vitro. When transfected as synthetic RNA ribozyme or as a synthetic RNA ribozyme stabilized by incorporation of 2-deoxycytosine and 2-deoxy-uracil analogs into peripheral blood CD3+ T cells, the ribozyme reduced levels of RIα protein to approximately 20% of control levels by removing the RIα mRNA. By this strategy, the majority of protein kinase A type 1 was removed from the T cells. We then assessed the immune responsiveness of CD3+ T cells transfected with ribozyme compared to control (mock) transfected T cells measured as T cell proliferation after activation of T cells by stimulation of the T cell receptor/CD3 complex (TCR/CD3). In order to simulate a T cell dysfunction as that of HIV infection, with elevated levels of cAMP and increased activation of protein kinase A type 1, we treated normal T cells with low dose (12.5 around $IC_{50}$) of the cAMP analog 8-(4-chlorophenyl)-thio-cAMPS (8-CPT-cAMP). As can be seen from FIG. 8, cAMP inhibited T cell proliferation to approximately 20% of control in mock transfected T cells. In contrast, T cells transfected with RIa ribozyme were only inhibited to approximately 40% by cAMP, i.e. a 2-fold increase in immune responsiveness in the presence of RIa ribozyme. This indicates that ribozymes to the RIa subunit of protein kinase A to inhibit production of protein kinase A type I (RIa), can be useful therapy to reverse the T cell dysfunction caused by activation of protein kinase A type I in immunodeficiencies. For in vivo use pretreatment of ribozymes to allow cellular uptake or introduction into cells as minigenes will be necessary.

Example 4

In order to abolish the increased signalling through protein kinase A type I in T cell dysfunction, we attempted to compete the localization of protein kinase A type I with the TCR/CD3 and thereby removing it from the substrate.

A peptide covering amino acids 493–515 of the A-kinase anchoring protein (AKAP) Ht31 (SEQ. ID. NO 2) has been shown to contain an amphipatic α-helix forming, a hydrophobic surface that represents the anchoring domain of both RII- and also RI anchoring AKAPs and the interacts with the R subunit binding domain. Recent data now show that the binding, of R.Icc is to dual-specificity AKAPs (D-AKAPl and DAKAP2 and that binding, of both RI and RII to AKAPs can be competed with the Ht31 competitor peptide in vitro. However, RI binds with much lower affinity than RII to AKAPs. Consequently, lower concentrations are expected to compete RI-mediated effects that RII-mediated effects in cell cultures.

We incubated blood CD3+ T cells with increasing concentrations of Ht31 (SEQ. ID. NO 2) peptide. In order to facilitate uptake, cells were treated with liposomes in the presence or absence of-peptide. The optimal concentrations of DOTAP liposomes and anti-CD3 antibody were titrated carefully in order to maintain the membrane stability and normal TCR/CD3-dependent activation of the T cells. Cells were incubated for 20 hours with DOTAP/peptide and incubations continued in the absence (solid bars) or presence of 8-CPT-cAMP (6.25 µM, hatched bars) and activated to proliferation by stimulation of TCR/CD3 T cell immune responsiveness was assessed as [3H]thymidine incorporation. The results (FIG. 9) show that in T cells treated with cAMP to simulate the situation of increased activation of protein kinase A type I in immunodeficiency, increasing concentrations of Ht-3 I peptide reversed the cAMP dependent inhibition of T cell proliferation (3-fold increased proliferation with cAMP in the presence of 50 µM Ht-31 compared to mock transfection). This indicates that competitor peptide could normalize the immune responses of dysfunctional T cells with elevated levels of cAMP.

A peptide (Ht-31P) where the amphipatic helix has been distorted by substitution of two valine residues with prolines served as a control right panel. In this case, treatment with increasing, concentrations of peptide did not increase the proliferation in the presence of cAMP.

Next, the effect of the competitor peptide (Ht-31, 35 µM) on T cell proliferation was examined in the presence of increasing concentrations of 8-CPT-cAMP and compared to mock transfected cells treated with the same concentrations of 8-CPT-cAMP (FIG. 10). As shown previously for normal peripheral blood T cells. Examples 1 and 2, FIGS. 1 and 4B), 8-CPT-cAMP inhibited also mock transfected cells in a positive cooperative fashion with an IC, around 1.8 µM (the lower $IC_{50}$ compared to untransfected cells in probably due to increased permeability with liposomes). In the presence of Ht-31 competitor peptide, a right-shifted inhibition curve by cAMP was observed with an apparent $IC_{50}$ of 4.8 µM. Compared to the left-shifted curves observed with T cells from HIV-infected patients or patients with CIV due to elevated levels of endogenous cAMP activating PKA type 1, the right-shift observed here would be expected to normalize the situation in patients.

In summary the results demonstrate that competition of the localization of protein kinase A type I with the TCR/CD3) to remove it from the substrate, can be a useful therapy to reverse the T cell dysfunction caused by activation of protein kinase A type I in immunodeficiencies.

REFERENCES

1. G. M. Kammer, Immunol. Today 9,22–2 (1988).
2. B. S. Skålhegg, et al, J. Biol. Chem. 267, 15707 (1992).
3. S. Skålhegg, et al, Science 263, 84 (1994).
4. B. Hofmann, P. Nishanlan, T. Nguyen, P. Insixiengmay, J. L. Fahey, Proc. Natl. Acad. Sci. U.S.A. 90, 6676 (1993).
5. S. Haraguchi, R. A. Good, N. K. Day, Immunol. Today 16, 595 (1995).
6. M. A. Nokta, R. B. Pollard, AIDS Res. Hum. Retroviruses 8, 1255 (1992).
7. Center for disease control and prevention: 1993 revised classification for HIV infection and expanded surveillance case definition for AIDS among adolescents and adults. MMWR 41, 1 (1992).
8. Gjertsen, B. T. et al., J. Biol. Chem. 270, 20599–20607 (1995).
9. Hammer, S. M., N. Engl. J. Med, 337, 725–3)$_{33}$) (1997).
10. Gulick, R. M., Treatment with indinavir, zidovudine, and lamivudine in adults with human immunodeficiency virus infection and prior antiretroviral therapy. N. Engl. J. Med. 337, 734–739.
11. Aukrust, P., Blood. 86:1383–1391 (1995).
12. Aukrust, P. et al., Clin. Exp. Immunol. 89:211–216 (1992).
13. Waldman, T. A., J. Biol. Chem. 266:2681–2684 (1991)
14. Eisenstein, E. M., J. S. Jaffe and W. Strober, J. Clin. Immunol. 13:247–258 (1993).
15. Cunningham-Rundles et al., N. Enal. J. Med. 33) 1:918–92–1 (1994).
16. Anastasiou, E. D. et al., J. Immunol. 148:2845–2852 (1992).
17. Munoz, E., J. Exp. Med. 172:95–103) (1990).

The invention claimed is:

1. A pharmaceutical composition useful for treating humans comprising:
   (A) a pharmaceutically effective amount of a cAMP antagonist, wherein said cAMP antagonist is selected from the group consisting of Rp-8-Br-monobutyryl-cAMPS and Rp-monobutyryl-cAMPS; and
   (B) a pharmaceutically acceptable adjuvant or filler.

2. A method for enhancing T cell proliferation in a subject afflicted with HIV or AIDS, comprising administering to said subject a pharmaceutical composition comprising:
   (A) a pharmaceutically effective amount of a specific inhibitor of PKA RIα$_2$C$_2$ isozyme, wherein said inhibitor is a cAMP antagonist and is a thio-substituted cAMP analog which is an equatorial diastereomer of 8-substituted 3',5' cyclic adenosine monophosphorothioate (Rp-8-substituted-cAMPS), and wherein said thio-substituted cAMP analog binds to an RIα subunit of said isozyme and acts as a selective or specific antagonist of said isozyme; and
   (B) a pharmaceutically acceptable adjuvant or filler.

3. The method of claim 1, wherein said cAMP antagonist is selected from the group consisting of Rp-8-Br-cAMPS, Rp-8-Br-monobutyryl-cAMPS, Rp-monobutyryl-cAMPS, Rp-8-(4-chlorophenyl-thio)-cAMPS, Rp-piperidino-cAMPS, and Rp-8Cl-cAMPS.

4. The method of claim 2, wherein said cAMP antagonist is selected from the group consisting of Rp-8-Br-cAMPS and Rp-8-Cl-cAMPS.

* * * * *